US007618637B2

(12) United States Patent
Rothman et al.

(10) Patent No.: US 7,618,637 B2
(45) Date of Patent: *Nov. 17, 2009

(54) HEAT SHOCK PROTEIN-BASED VACCINES AND IMMUNOTHERAPIES

(75) Inventors: James Rothman, New York, NY (US); F. Ulrich Hartl, Kottgeisering (DE); Mee H. Hoe, New York, NY (US); Alan Houghton, New York, NY (US); Yoshizumi Takechi, Kobe (JP); Mark Mayhew, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 346 days.

This patent is subject to a terminal disclaimer.

(21) Appl. No.: 10/170,738

(22) Filed: Jun. 13, 2002

(65) Prior Publication Data

US 2008/0274128 A1   Nov. 6, 2008

Related U.S. Application Data

(60) Continuation of application No. 09/552,868, filed on Apr. 20, 2000, now Pat. No. 6,761,892, which is a division of application No. 09/011,645, filed as application No. PCT/US96/13363 on Aug. 16, 1996, now Pat. No. 6,663,868.

(60) Provisional application No. 60/002,490, filed on Aug. 18, 1995.

(51) Int. Cl.
*A61K 39/385* (2006.01)

(52) U.S. Cl. .............................. 424/193.1; 424/196.11; 424/277.1; 424/278.1; 530/300

(58) Field of Classification Search ............... 424/184.1
See application file for complete search history.

(56) References Cited

U.S. PATENT DOCUMENTS

| | | | |
|---|---|---|---|
| 5,149,529 A * | 9/1992 | Ho et al. ................. | 424/196.11 |
| 5,348,945 A | 9/1994 | Berberian et al. | |
| 5,498,538 A | 3/1996 | Kay et al. | |
| 5,541,109 A | 7/1996 | Searfoss | |
| 5,679,352 A | 10/1997 | Chong et al. | |
| 5,750,119 A | 5/1998 | Srivastava | |
| 5,837,251 A | 11/1998 | Srivastava | |
| 5,935,576 A | 8/1999 | Srivastava | |
| 5,961,979 A | 10/1999 | Srivastava | |
| 5,962,262 A | 10/1999 | Hillman et al. | |
| 5,985,270 A | 11/1999 | Srivastava | |
| 5,997,873 A | 12/1999 | Srivastava | |
| 6,017,540 A | 1/2000 | Srivastava et al. | |
| 6,030,618 A | 2/2000 | Srivastava | |
| 6,048,530 A | 4/2000 | Srivastava | |
| 6,127,393 A | 10/2000 | Fernandex-Pol | |
| 6,331,299 B1 | 12/2001 | Rothman et al. | |
| 6,641,812 B2 * | 11/2003 | Rothman et al. ......... | 424/184.1 |
| 6,656,679 B2 * | 12/2003 | Rothman et al. ............ | 435/5 |
| 6,663,868 B1 | 12/2003 | Rothman et al. | |
| 6,673,348 B2 * | 1/2004 | Rothman et al. ......... | 424/184.1 |
| 6,719,974 B1 | 4/2004 | Rothman et al. | |
| 6,761,892 B1 | 7/2004 | Rothman et al. | |
| 6,773,707 B1 | 8/2004 | Rothman et al. | |
| 7,309,491 B2 | 12/2007 | Slusarewicz et al. | |
| 7,420,037 B2 | 9/2008 | Slusarewicz et al. | |
| 2003/0185842 A1 | 10/2003 | Rothman et al. | |
| 2003/0185843 A1 | 10/2003 | Rothman et al. | |
| 2004/0043419 A1 | 3/2004 | Rothman et al. | |
| 2004/0071720 A1 | 4/2004 | Rothman et al. | |
| 2004/0071721 A1 | 4/2004 | Rothman et al. | |
| 2004/0071722 A1 | 4/2004 | Rothman et al. | |
| 2004/0071723 A1 | 4/2004 | Rothman et al. | |
| 2004/0071724 A1 | 4/2004 | Rothman et al. | |
| 2004/0071725 A1 | 4/2004 | Rothman et al. | |
| 2004/0101532 A1 | 5/2004 | Houghton et al. | |
| 2004/0127684 A1 | 7/2004 | Rothman et al. | |
| 2005/0202033 A1 | 9/2005 | Flechtner et al. | |

FOREIGN PATENT DOCUMENTS

| | | |
|---|---|---|
| EP | 0 538 952 | 4/1993 |
| WO | WO 89/04871 | 6/1989 |
| WO | WO 93/03766 A1 | 3/1993 |
| WO | WO 93/17712 | 9/1993 |
| WO | WO 94/11513 | 5/1994 |
| WO | WO 94/29459 | 12/1994 |
| WO | WO 95/24923 * | 9/1995 |
| WO | WO 96/10411 | 4/1996 |
| WO | WO 97/06281 | 2/1997 |
| WO | WO 97/06685 | 2/1997 |
| WO | WO 97/06821 | 2/1997 |
| WO | WO 97/10000 | 3/1997 |
| WO | WO 97/10001 | 3/1997 |
| WO | WO 97/10002 | 3/1997 |
| WO | WO 97/26910 | 7/1997 |
| WO | WO 98/23735 | 6/1998 |
| WO | WO 98/35705 | 8/1998 |
| WO | WO 99/22761 A1 | 5/1999 |
| WO | WO 99/42121 | 8/1999 |

OTHER PUBLICATIONS

Blond-Elguindi et al. Affinity Panning of a Library of Peptides Displayed on Bacteriophages Reveals the Binding Specificity of BiP. (1993) Cell, vol. 75, 717-728.*

(Continued)

*Primary Examiner*—Bruce Campell
*Assistant Examiner*—Agnieszka Boesen
(74) *Attorney, Agent, or Firm*—Jones Day

(57) ABSTRACT

The present invention relates to methods and compositions for inducing an immune response in a subject, wherein the subject is administered an effective amount of at least one heat shock protein in combination with one or more defined target antigens. These methods and compositions may be used in the treatment of infectious eases and cancers.

48 Claims, 5 Drawing Sheets

OTHER PUBLICATIONS

Banks et al. Recognition by a nd in Vitro Induction of Cytotoxic T Lymphocytes against Predicted Epitopes of the Immediate Early Protein ICP27 of Herpes Simplex Virus. (1993) Journal of Virology, vol. 67, 613-616.*
Tavaria et al. A hitchiker's guide to the human Hsp70 family. (1996) vol. 1, 23-28.*
Blond-Elguindi et al. (Cell, 1993, vol. 75, p. 717-728).*
Auger et al. (Nature Medicine, 1996, vol. 2, p. 306-310).*
Anderson, "Human gene therapy", Nature 392(6679 Suppl):25-30 (1998).
Blachere et al., "Heat shock protein vaccines against cancer", J. Immunother. 14(4):352-356 (1993).
Castelli et al., "Human heat shock protein 70 peptide complexes specifically activate antimelanoma T cells", Cancer Res. 61(1):222-227 (2001).
Chen et al., "Enhancement of DNA vaccine potency by linkage of antigen gene to an HSP70 gene", Cancer Res. 60(4):1035-1042 (2000).
Fedoseyeva et al., "CD4+ T cell responses to self- and mutated p53 determinants during tumorigenesis in mice", J. Immunol. 164(11):5641-5651 (2001).
Flajnik et al., Which came first, MHC Class I or Class II?, Immunogenetics 33:295-300 (1991).
Heike et al., "Heat shock protein-peptide complexes for use in vaccines", J. Leukoc. Biol. 60(2):153-158 (1996).
Heikema et al., "Generation of heat shock protein-based vaccines by intracellular loading of gp96 with antigenic peptides", Immunol. Lett. 57(1-3):69-74 (1997).
Hinds et al., "Immunological evidence for the association of p53 with a heat shock protein, hsc70, in p53-plus-ras-transformed cell lines", Mol Cell Biol. 7(8):2863-2869 (1987).
Huang et al., "In Vivo Cytotoxic T Lymphocytes Elicitation by Mycobacterial Heat Shock Protein 70 Fusion Proteins Maps to a Discrete Domain and Is CD4.sup.30 T Cell Independent", J. Exp. Med. 191:403-408 (2000).
Konen-Waisman et al., "Self heat-shock protein (hsp60) peptide serves in a conjugate vaccine against a lethal pneumococcal infection", J. Infect. Dis. 179(2):403-413 (1999).
Lewis et al., "Pilot study of vaccination with autologous tumor-derived gp96 heat shock protein-peptide complex(HSPPC-96) in patients with resected pancreatic adenocarcinoma", Meeting Abstract, Proceedings of the Annual Meeting of the American Society of Clinical Oncology, 18:A1687 (1999).
Lopez-Guerrero et al., "Modulation of adjuvant arthritis in Lewis rats by recombinant vaccinia virus expressing the human 60-kilodalton heat shock protein", Infect. Immun. 61(10):4225-4231 (1993).
Lovett et al., Rubella virus-specific cytotoxic T-lymphocyte responses: identification of the capsid as a target of major histocompatibility complex class I-restricted lysis and definition of two epitopes, J. Virol. 67(10):5849-5858 (1993).
Melcher et al., Tumor Immonogenicity is Determined by the Mechanism of Cell Death Via Induction of Heat Shock Protein Expression, Nature Medicine 4:581-587 (1998).
Meng et al., "Tumor suppressor gene as targets for cancer therapy", in: *Gene Therapy of Cancer*, Lattime and Gerson, Eds., Academic Press, Chap. 1, pp. 3-20 (1999).
Ngo et al., "Computational Complexity Protein Structure Prediction and the Levinthal Paradox", Birkhauser Boston, vol. 14, pp. 491-495 (1994).
Nilsson et al., "Fusion proteins in biotechnology and structural biology", Curr. Opin. Struct. Biol. 2:569-575 (1992).
Riddell et al., "T-cell mediated rejection of gene-modified HIV-specific cytotoxic T lymphocytes in HIV-infected patients", Nature Medicine 2:216-223 (1996).
Srivastava and Udono, "Heat shock protein-peptide complexes in cancer immunotherapy", Curr. Opin. Immunol. 6(5):728-732 (1994).
Suzuki et al., "Regulating the retention of T-cell receptor alpha chain variants within the endoplasmic reticulum: Ca(2+)-dependent association with BiP", J. Cell Biol. 114:189-205 (1991).
Theobald et al., "Targeting p53 as a general tumor antigen", Proc. Natl. Acad. Sci. USA 92(26):11993-11997 (1995).
Thomson et al., "Minimal epitopes expressed in a recombinant polyepitope protein are processed and presented to CD8+ cytotoxic T cells: implications for vaccine design", Proc. Natl. Acad. Sci. USA 92(13):5845-5849 (1995).
Thomson et al., "Recombinant polyepitope vaccines for the delivery of multiple CD8 cytotoxic T cell epitopes", J. Immunol. 157(2):822-6 (1996).
Todryk et al., "Heat Shock Protein 70 Induced During Tumor Cell Killing Induces Th1 Cytokines and Targets Immature Dendritic Cell Precursors to Enhance Antigen Uptake", J. Immunol. 163:1398-1408 (1999).
Verma et al., "Gene therapy—promises, problems and prospects", Nature 389(6648):239-242 (1997).
Wells et al., "Hsp72-mediated Augmentation of MHC Class I Surface Expression and Endogenous Antigen Presentation", Int. Immunol 10:609-617 (1998).
Yamazaki et al., "Cutting Edge: Tumor Secreted Heat Shock-Fusion Protein Elicits CD8 Cells for Rejection", J. Immunol. 163:5178-5182 (1999).
Fourie et al., 1994, "Common and divergent peptide binding specificities of hsp70 molecular chaperones." J. Biological Chemistry 269:30470-30478.
Auger et al., 1996, Nature Medicine 2:306-310.
Giboa, 1996, Seminars in Oncology 23:101-107.
Minami et al., 1996, J. Biol. Chem. 271:19617-19624.
Nieland et al., 1996, Proc. Natl. Acad. Sci. USA 93:6135-6139.
Zhu et al., 1996, Science 272:1606-1614.
Bauer et al., 1995, Scan. J. Immunol. 42:317-323.
Blachere and Srivastava, 1995, Seminars in Cancer Biology 6:349-355.
Edginton, 1995, Bio/Technol. 13:1442-1444.
Greene et al., 1995, J. Biol. Chem. 270-2967-2978.
Hohfeld et al., 1995, Cell 83:589-598.
Lowrie et al., 1995, J. Cell. Biochem, Suppl. 0(19b):220.
McCarty et al., 1995, J. Mol. Biol. 249:126-137.
Multhoff et al., 1995, Int. J. Cancer 61:272-279.
Zhu et al., 1995, Scand. J. Immunol. 42:557-563.
Barrios et al., 1994, Clin. Exp. Immunol. 98:224-228.
Barrios et al., 1994, Clin. Exp. Immunol. 98:229-233.
Del Guidice, 1994, Experientia 50:1061-1066.
Lowrie et al., 1994, Vaccine 12:1537-1540.
Nygren et al., 1994, Trends Biotechnol. 12(5):184-188.
Retzlaff et al., 1994, Infect. Immun. 62:5689-5693.
Schmid et al., 1994, Science 263:971-973.
Sato et al., 1994, Proc. Annu. Meet. Am. Assoc. Cancer Res. 35:A2959.
Silva and Lowrie, 1994, Immunology 82:244-248.
Srivastava, 1994, Experentia 50:1054-1060.
Srivastava and Udono, 1994, Current Opinion in Immunology 6:728-732.
Blond-Elguindi et al., 1993, Cell 75: 717-728.
DeNagel and Pierce et al., 1993, Critical Reviews in Immunology 13:71:81.
Lukacs et al., 1993, J. Exp. Med. 178:343-348.
Mustafa et al., 1993, Infection and Immunity 61:5294-5301.
Palleros et al., 1993, Nature 365:664-666.
Perraut, 1993, Clin. Exp. Immunol. 93:382-386.
Srivastava, 1993, Adv. Cancer Res. 62:153-177.
Yamamoto et al., 1993 Infection and Immunity 61:2154-2161.
Barrios et al., 1992, Euro. J. Immunol. 22:1365-1372.
Davidoff et al., 1992, Proc. Natl. Acad. Sci. USA 89:3439-3442.
Pidoux et al., 1992, EMBO J. 11:1583-1591.
Lussow et al., 1991, J. Eur. Immunol. 21:2297-2302.
Srivastava and Maki, 1991, Current Topics in Microbiology and Immunology 167:109-123.
Flynn et al., 1989, Science 245:385-390.
Pelham 1988, EMBO J. 7:913-918.
Munro and Pelham, 1987, Cell, 480:899-907.
Srivastava et al., 1986, Proc. Natl. Acad. Sci. USA 83:3407-3411.
Ullrich et al., Proc. 1986, Natl. Acad. Sci. USA 83:3121-3125.
Von Heijne, 1985, J. Mol. Biol. 184:99-105.
Suzue, K. et al., 1996, J. Immunol. 156:873-9.
Jindal, S., 1996, Trends Biotechnol. 14:17-20.

Arnold, D. et al., 1995, J. Exp. Med. 182:885-9.
Suto, R. et al., 1995, Science 269:1585-7.
Gething, M.-J. et al., 1995, Cold Spring Harb. Symp. Quant. Biol. 60:417-28.
Tarpey, I. et al., 1994, Immunology 81:222-7.
Udono, H. et al., 1994, Science 91:3077-81.
Li, Z. et al., 1993, EMBO J. 12:3143-51.
Udono, H. et al., 1993, J. Exp. Med. 178:1391-6.
Moroi, Y., 2000, Proc Natl Acad Sci U S A Mar. 28, 2000;97(7):3485-90.
Melnick, J., 1992, Journal of Biochemistry 267:21303-21306.
Galigniana et al., 1998, Mol. Endo. 12:1903-1913.
Czar et al., 1997, Biochemistry 36:7776-7785.
Blachere et al., 1997, J. Exp. Med. 186:1315-1322.
Tamura et al., 1997, Science 278:117-120.
Wearsch et al., 1997, J. Biol. Chem. 272:5152-5156.
Tavaria et al., 1996, Cell Stress and Chaperones 1:23-28.
Jakob et al., 1996, J. Biol. Chem. 271:10035-10041.
Rosenberg et al., Dec. 1996, inNovations (newsletter of Novagen, Inc.) No. 6, pp. 1-6.
Whitesell, et al., 1994, Proc. Natl. Acad. Sci. USA 91:8324-8328.
Gragerov et al., 1994, J. Mol. Biol. 235:133-135.
Gragerov et al., 1994, J. Mol. Biol. 235:848-854.
Nadeau et al., 1992, J. Biol. Chem. 268:1479-1487.
Nadeau et al., 1992, Protein Science 1:970-979.
Dillman et al., 1995, J. Cell. Biochem., Suppl. 19B, p. 190.
Plumier et al., 1995, J. Clin. Invest. 95 (4), pp. 1854-1860.
Little, et al., 1994, Critical Reviews in Eukaryotic Gene Expression, 1994 4(1) p. 1-18.
Porgador et al., 1994 Nat. Immun. 13:113-130.
Jaattela, 1995, Int. J. Cancer, 60 (5), pp. 689-693.
Udono et al., 1994, J. Immun. 152, pp. 5398-5403.

Pardoll. 1993, Current Opinion in Immunology, 5:719-725.
Mastrangelo et al., 1996, Seminars in Oncology, 23:4-21.
Lukacs et al., 1994, Cancer Gene Therapy, 1:217.
Office Action; U.S. Appl. No. 09/011,645, date mailed: Feb. 13, 2002.
Office Action; U.S. Appl. No. 09/552,868, date mailed: Feb. 13, 2002.
Office Action; U.S. Appl. No. 09/636,295, date mailed: Apr. 23, 2002.
Office Action; U.S. Appl. No. 09/680,806, date mailed: Apr. 23, 2002.
Office Action; U.S. Appl. No. 09/794,529, date mailed: Jan. 15, 2003.
Office Action; U.S. Appl. No. 09/794,832, date mailed: Jan. 15, 2003.
Office Action; U.S. Appl. No. 09/794,517, date mailed: Jan. 15, 2003.
Office Action; U.S. Appl. No. 10/258,147, date mailed: Nov. 15, 2004.
Office Action; U.S. Appl. No. 10/258,147 date mailed: Nov. 24, 2006.
Office Action; U.S. Appl. No. 10/258,147 date mailed: Jun. 27, 2007.
Partidos et al., 1996, "Structural requirements for synthetic immunogens to induce measles virus specific CTL responses," Mol. Immun., vol. 33(16):1223-1229.
Shirai et al., 1994, "Helper-cytotoxic T lymphocyte (CTL) determinant linkage required for priming of anti-HIV CD8$^+$ CTL in vivo with peptide vaccine constructs," J of Immun., vol. 152:549-556.
Davenport et al., 1995, "Naturally processed peptides from two disease-resistance-associated HLA-DR13 alleles show related sequence motifs and the effects of the dimorphism at position 86 of the HLA-DR beta chain." Proc. Natl. Acad. Sci. 92:6567-6571.
Falk et al., 1991, "Allele-specific motifs revealed by sequencing of self-peptides eluted from MHC molecules." Nature 351: 290-296.
Flynn et al, 1991, "Peptide-binding specificity of the molecular chaperone BiP." Nature 353: 726-730.

* cited by examiner

HEAT SHOCK PROTEIN-BASED VACCINES AND IMMUNOTHERAPIES

The invention described herein was made in the course of work under NIH Core Grant No. CA 08748. The United States government may have certain rights in this invention.

INTRODUCTION

The present invention relates to methods and compositions for inducing an immune response in a subject, wherein the subject is administered an effective amount of at least one heat shock protein in combination with one or more defined target antigens. These methods and compositions may be used in the treatment of infectious diseases and cancers.

BACKGROUND OF THE INVENTION

Heat shock proteins were originally observed to be expressed in increased amounts in mammalian cells which were exposed to sudden elevations of temperature, while the expression of most cellular proteins is significantly reduced. It has since been determined that such proteins are produced in response to various types of stress, including glucose deprivation. As used herein, the term "heat shock protein" will be used to encompass both proteins that are expressly labeled as such as well as other stress proteins, including homologs of such proteins that are expressed constitutively (i.e., in the absence of stressful conditions). Examples of heat shock proteins include BiP (also referred to as grp78), hsp/hsc70, gp96 (grp94), hsp60, hsp40 and hsp90.

Heat shock proteins have the ability to bind other proteins in their non-native states, and in particular to bind nascent peptides emerging from ribosomes or extruded into the endoplasmic reticulum. Hendrick and Hartl., *Ann. Rev. Biochem.* 62:349-384 (1993); Hartl., *Nature* 381:571-580 (1996). Further, heat shock proteins have been shown to play an important role in the proper folding and assembly of proteins in the cytosol, endoplasmic reticulum and mitochondria; in view of this function, they are referred to as "molecular chaperones". Frydman et al., *Nature* 370: 111-117 (1994); Hendrick and Hartl., *Ann. Rev. Biochem.* 62:349-384 (1993); Hartl, *Nature* 381:571-580 (1996).

For example, the protein BiP, a member of a class of heat shock proteins referred to as the hsp70 family, has been found to bind to newly synthesized, unfolded p immunoglobulin heavy chain prior to its assembly with light chain in the endoplasmic reticulum. Hendershot et al., *J. Cell Biol.* 104: 761-767 (1987). Another heat shock protein, gp96, is a member of the hsp90 family of stress proteins which localize in the endoplasmic reticulum. Li and Srivastava, *EMBO J.* 12:3143-3151 (1993); Mazzarella and Green, *J. Biol. Chem.* 262:8875-8883 (1987). It has been proposed that gp96 may assist in the assembly of multi-subunit proteins in the endoplasmic reticulum. Wiech et al., *Nature* 358:169-170 (1992).

It has been observed that heat shock proteins prepared from tumors in experimental animals were able to induce immune responses in a tumor-specific manner; that is to say, heat shock protein purified from a particular tumor could induce an immune response in an experimental animal which would inhibit the growth of the same tumor, but not other tumors. Srivastava and Maki, 1991, *Curr. Topics Microbial.* 167:109-123 (1991). The source of the tumor-specific immunogenicity has not been confirmed. Genes encoding heat shock proteins have not been found to exhibit tumor-specific DNA polymorphism. Srivastava and Udono, *Curr. Opin. Immunol.* 6:728-732 (1994). High resolution gel electrophoresis has indicated that gp96 may be heterogeneous at the molecular level. Feldweg and Srivastava, *Int. J. Cancer* 63: 310-314 (1995). Evidence suggests that the source of heterogeneity may be populations of small peptides adherent to the heat shock protein, which may number in the hundreds. Id. It has been proposed that a wide diversity of peptides adherent to tumor-synthesized heat shock proteins may render such proteins capable of eliciting an immune response in subjects having diverse HLA phenotypes, in contrast to more traditional immunogens which may be somewhat HLA-restricted in their efficacy. Id.

Recently, Nieland et al. (*Proc. Natl. Acad. Sci. U.S.A.* 93:6135-6139 (1996)) identified an antigenic peptide containing a cytotoxic T lymphocyte (CTL) vesicular stomatitis virus (VSV) epitope bound to gp96 produced by VSV-infected cells. Neiland's methods precluded the identification of any additional peptides or other compounds which may also have bound to gp96, and were therefore unable to further characterize higher molecular weight material which was bound to gp96 and detected by high pressure liquid chromatography.

It has been reported that a synthetic peptide comprising multiple iterations of NANP (Asp Ala Asp Pro) malarial antigen, chemically cross-linked to glutaraldehyde-fixed mycobacterial hsp65 or hsp70, was capable of inducing antibody formation (i.e., a humoral response) in mice in the absence of any added adjuvant; a similar effect was observed using heat shock protein from the bacterium *Escherichia coli*. Del Guidice, *Experientia* 50:1061-1066 (1994); Barrios et al., *Clin. Exp. Immunol.* 98:224-228 (1994); Barrios et al., *Eur. J. Immunol.* 22:1365-1372 (1992). Cross-linking of synthetic peptide to heat shock protein and possibly glutaraldehyde fixation was required for antibody induction. Barrios et al., *Clin. Exp. Immunol.* 98:229-233.

It has now been discovered, according to the present invention, that heat shock protein may be combined with target antigen and used to induce an immune response which includes a cytotoxic cellular component, i.e., a cellular response.

SUMMARY OF THE INVENTION

The present invention relates to methods and compositions for inducing an immune response in a subject, wherein at least one heat shock protein in combination with one or more defined target antigens is administered to the subject.

Unlike prior disclosures relating to heat shock protein associated with an undefined population of potential antigens which have been restricted, in their immunogenic effect, to a single tumor, the present invention provides for methods and compositions which combine heat shock protein with a defined target antigen which may be selected on the basis that it is immunogenic in diverse occurrences of a neoplastic or infectious disease, or because it has been identified, in an individual instance, as being particularly immunogenic. Further, because the use of one or more defined target antigen permits more control over the immune response elicited, it may avoid the induction of an undesirable immune response.

In alternative embodiments of the invention, the target antigen may be either (i) an antigen which itself binds to the heat shock protein; or (ii) a hybrid antigen comprising an immunogenic domain as well as a heat shock protein-binding domain. The immunogenic domain may be an entire protein or peptide antigen, or may be only a portion of the selected antigen, for example a selected epitope of the antigen. In specific, nonlimiting embodiments of the invention, the heat shock protein binding domain may comprise a peptide having the sequence:

His Trp Asp Phe Ala Trp Pro Trp [SEQ. ID NO. 1]

The present invention provides for methods of administering such heat shock protein/target antigen compositions comprising (i) combining one or more heat shock protein with one or more target antigens in vitro, under conditions wherein binding of target antigen to heat shock protein occurs to form a target antigen/heat shock protein complex; and (ii) administering the target antigen, bound to heat shock protein, in an effective amount to a subject in need of such treatment.

Alternatively, heat shock protein/target antigen combinations of the invention may be administered to a subject by introducing nucleic acid encoding the heat shock protein and the target antigen into the subject such that the heat shock protein and target antigen bind in situ.

DETAILED DESCRIPTION OF THE INVENTION

Figure 1:
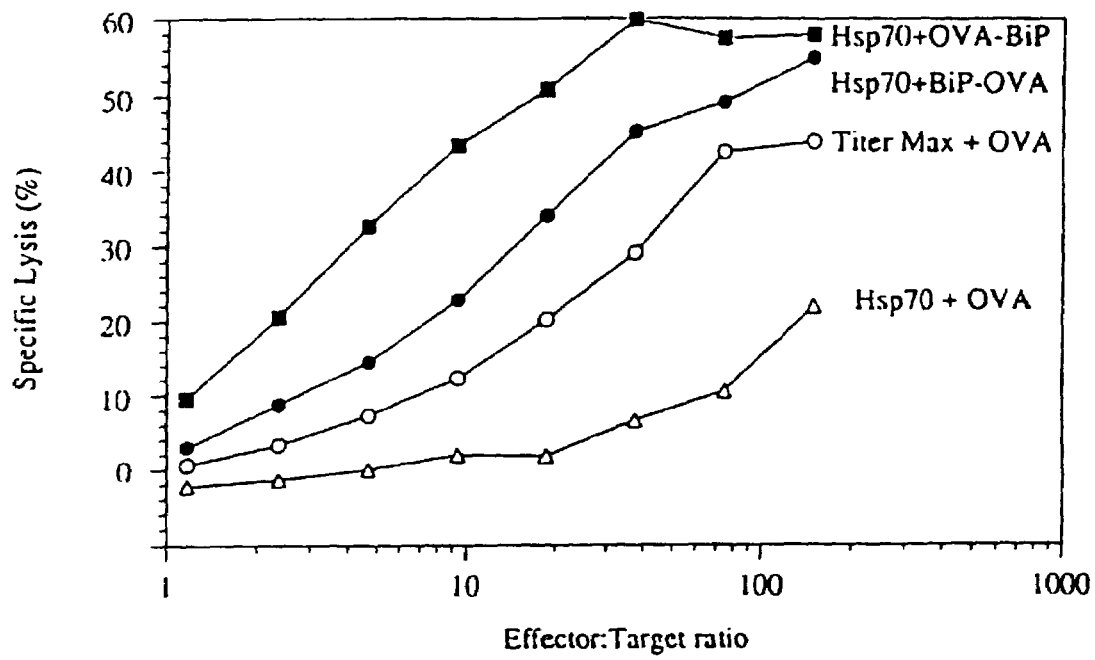
FIG. 1 shows the induction of a cellular immune response using hybrid peptide antigens in accordance with the invention.

For purposes of clarity of description, and not by way of limitation, the detailed description is divided into the following subsections:

(i) heat shock proteins;
(ii) target antigens; and
(iii) methods of administration.

Heat Shock Proteins

The term "heat shock protein", as used herein, refers to any protein which exhibits increased expression in a cell when the cell is subjected to a stress. In preferred nonlimiting embodiments, the heat shock protein is originally derived from a eukaryotic cell; in more preferred embodiments, the heat shock protein is originally derived from a mammalian cell. For example, but not by way of limitation, heat shock proteins which may be used according to the invention include BiP (also referred to as grp78), hsp/hsc70, gp96(grp94), hsp60, hsp40, and hsp90. Especially preferred heat shock proteins are BiP, gp96, and hsp70, as exemplified below. Naturally occurring or recombinantly derived mutants of heat shock proteins may also be used according to the invention. For example, but not by way of limitation, the present invention provides for the use of heat shock proteins mutated so as to facilitate their secretion from the cell (for example having mutation or deletion of an element which facilitates endoplasmic reticulum recapture, such as KDEL or its homologs; such mutants are described in concurrently filed PCT Application No. PCT/US96/13233 (Attorney Docket No. MSK.P-018), which is incorporated herein by reference.

For embodiments of the invention wherein heat shock protein and target antigen are directly administered to the subject in the form of a protein/peptide complex, the heat shock protein may be prepared, using standard techniques, from natural sources, for example as described in Flynn et al., *Science* 245: 385-390 (1989), or using recombinant techniques such as expression of a heat shock encoding vector in a suitable host cell such as a bacterial, yeast or mammalian cell. If pre-loading of the heat shock protein with peptides from the host organism is a concern, the heat shock protein can be incubated with ATP and then repurified. Nonlimiting examples of methods for preparing recombinant heat shock proteins are set forth below.

A nucleic acid encoding a heat shock protein may be operatively linked to elements necessary or desirable for expression and then used to express the desired heat shock protein as either a means to produce heat shock protein for use in a protein vaccine or, alternatively, in a nucleic acid vaccine. Elements necessary or desirable for expression include, but are not limited to, promoter/enhancer elements, transcriptional start and stop sequences, polyadenylation signals, translational start and stop sequences, ribosome binding sites, signal sequences and the like. For example, but not by way of limitation, genes for various heat shock proteins have been cloned and sequenced, including, but not limited to, gp96, human: Genebank Accession No. X15187; Maki et al., *Proc. Nat'l Acad. Sci.* 87: 5658-5562 (1990), mouse: Genebank Accession No. M16370; Srivastava et al., *Proc. Nat'l Acad. Sci.* 84:3807-3811 (1987)); BiP, mouse: Genebank Accession No. U16277; Haas et al., Proc. Nat'l Acad. Sci. U.S.A. 85: 2250-2254 (1988), human: Genebank Accession No. M19645; Ting et al., DNA 7: 275-286 (1988); hsp70, mouse: Genebank Accession No. M35021; Hunt et al., *Gene* 87: 199-204 (1990), human: Genebank Accession No. M24743; Hunt et al., Proc. Nat'l Acad. Sci. U.S.A. 82: 6455-6489 (1995); and hsp40 human: Genebank Accession No. D49547; Ohtsuka K., *Biochem Biophys. Res. Commun.* 197: 235-240 (1993).

Target Antigens

A target antigen, according to the invention, may be either (i) an antigen which itself binds to the heat shock protein; or (ii) a hybrid antigen comprising an immunogenic domain as well as a heat shock protein-binding domain. Thus, the target antigen serves at least two functions, namely (I) it contains an epitope capable of inducing the desired immune response; and (ii) it is capable of physically binding to its partner heat shock protein. Of note, the term "physically binds" indicates that the target antigen and heat shock protein exhibit a physical interaction which permits the adherence of one to the other for at least a transient period of time; of note, the binding need not, and in most embodiments of the invention should not, be irreversible.

In certain embodiments, an antigen capable of inducing the desired immune response may be found to be inherently capable of binding to a partner heat shock protein. In other embodiments, it may be necessary or desirable to link an immunogenic antigen to one or more other compounds so as to create a hybrid antigen which contains both an immunogenic domain as well as a heat shock protein binding domain. In such circumstances, a compound which is, itself, an immunogenic antigen may be linked to a compound which is, itself, capable of binding to a heat shock protein. Alternatively, the linkage of two or more compounds which individually lack either functionality may give rise to the desired immunogenic and binding characteristics.

The term "antigen" as used herein, refers to a compound which may be composed of amino acids, carbohydrates, nucleic acids or lipids individually or in any combination.

The term "target antigen", as used herein, refers to a compound which binds to one or more heat shock proteins and which is representative of the immunogen toward which an immune response is desirably directed. For example, where the immunogen is an influenza virus, the target antigen may be a peptide fragment of the matrix protein of the influenza virus. As used herein, the term "immunogen" is applied to the neoplastic cell, infected cell, pathogen, or component thereof, towards which an immune response is to be elicited, whereas the target antigen is a portion of that immunogen which can provoke the desired response and which inherently or through engineering binds to one or more heat shock proteins. In particular, the target antigen is selected to elicit an immune response to a particular disease or pathogen, including peptides obtained from MHC molecules, mutated DNA gene products, and direct DNA products such as those obtained from tumor cells.

While the invention may be applied to any type of immunogen, immunogens of particular interest are those associated with, derived from, or predicted to be associated with a neoplastic disease, including but not limited to a sarcoma, a lymphoma, a leukemia, or a carcinoma, and in particular, with melanoma, carcinoma of the breast, carcinoma of the prostate, ovarian carcinoma, carcinoma of the cervix, colon carcinoma, carcinoma of the lung, glioblastoma, astrocytoma, etc. Further, mutations of tumor suppressor gene products such as p53, or oncogene products such as ras may also provide target antigens to be used according to the invention.

In further embodiments, the immunogen may be associated with an infectious disease, and, as such, may be a bacterium, virus, protozoan, mycoplasma, fungus, yeast, parasite, or prion. For example, but not by way of limitation, the immunogen may be a human papilloma virus (see below), a herpes virus such as herpes simplex or herpes zoster, a retrovirus such as human immunodeficiency virus 1 or 2, a hepatitis virus, an influenza virus, a rhinovirus, respiratory syncytial virus, cytomegalovirus, adenovirus, *Mycoplasma pneumoniae*, a bacterium of the genus *Salmonella, Staphylococcus, Streptococcus, Enterococcus, Clostridium, Escherichia, Klebsiella, Vibrio, Mycobacterium*, amoeba, a malarial parasite, *Trypanosoma cruzi*, etc.

Immunogens may be obtained by isolation directly from a neoplasm, an infected cell, a specimen from an infected subject, a cell culture, or an organism culture, or may be synthesized by chemical or recombinant techniques. Suitable antigenic peptides, particularly for use in a hybrid antigen, for use against viruses, bacteria and the like can be designed by searching through their sequences for MHC class I restricted peptide epitopes containing HLA binding sequences such as but not limited to HLA-A2 peptide binding sequences:

Xaa(Leu/Met)XaaXaaXaa(Val/Ile/Leu/Thr)XaaXaa(Val/Leu) [SEQ ID No. 2],

Rammensee et al., *Immunogenetics* 41: 178-223 (1995),

Xaa(Leu/Met)XaaXaaXaaXaaXaaXaaVal [SEQ ID No. 3],

Tarpey, et al *Immunology* 81: 222-227 (1994),

Xaa(Val/Gln)XaaXaaXaaXaaXaaXaaLeu [SEQ ID No. 28]

Barouch et al., *J. Exp. Med.* 182: 1847-1856 (1995).

It may also be desirable to consider the type of immune response which is desired. For example, under certain circumstances, a humoral immune response may be appropriate. In other cases, and indeed where an immune response directed toward neoplastic cells or infected cells is sought to be elicited, a cellular immune response is particularly desirable. Accordingly, particular epitopes associated with the activation of B cells, T helper cells, or cytotoxic T cells may be identified and selected for incorporation into the target antigen.

It may also be desirable to utilize target antigen associated with an autoimmune disease or allergy. Such a target antigen may be administered, together with one or more heat shock proteins, in an amount sufficient to be tolerogenic or to inhibit a pre-existing immune response to the target antigen in a subject. The amount of heat shock protein required to inhibit the immune response is expected to be substantially greater than the amount required for stimulation.

Although the size of target antigen may vary depending upon the heat shock protein used, in nonlimiting embodiments of the invention, the target antigen may be the size of a peptide having between 4 and 500 of amino acid residues, and preferably be the size of a peptide having between 4 and 100, most preferably 7 and 20 amino acid residues. As such, it may be desirable to produce a fragment of an immunogen to serve as a target antigen, or, alternatively, to synthesize a target antigen by chemical or recombinant DNA methods. In some instances, however, an immunogen may, in intact form, serve as a target antigen.

Based on the foregoing considerations, a target antigen may be prepared, and then tested for its ability to bind to heat shock protein. In some instances, binding of target antigen to a particular heat shock protein may be facilitated by the presence of at least one other protein, which may be a heat shock protein.

For example, binding of target antigen to a heat shock protein may be evaluated by labeling the target antigen with a detectable label, such as a radioactive, fluorescent, enzymatic or pigmented label, combining the target antigen with heat shock protein under conditions which would be expected to permit binding to occur, and then isolating the heat shock protein while removing any unbound target antigen, and determining whether any labeled target antigen had adhered to the heat shock protein. As a specific example, and not by way of limitation, the ability of a target antigen to bind to BiP heat shock protein may be evaluated by combining 2 µg BiP with up to about 1150 pmole of radioactively labeled target antigen in buffer containing 50 mM Tris HCl (pH 7.5), 200 mM NaCl, and 1 mM $Na_2EDTA$, in a final volume of 50 µl, for 30 minutes at 37 degrees Centigrade. Unbound target antigen may then be removed from bound BiP-target antigen by centrifugation at long by desalting through a 1 ml Sephadex-G column for 2 minutes. Penefsky, *J. Biol. Chem.* 252:2891 (1977). To prevent binding to the resin, columns may first be treated with 100 µl of bovine serum albumin in the same buffer and centrifuged as above. Bound target antigen may then be quantitated by liquid scintillation counting. See Flynn et al., *Science* 245:385-390 (1989).

Because ATP hydrolysis drives the release of peptides from many known heat shock proteins, the amount of ATPase activity may often be used to quantitate the amount of target antigen binding to heat shock protein. An example of how such an assay may be performed is set forth in Flynn et al., *Science* 245:385-390 (1990).

If a particular immunogen or a fragment thereof does not satisfactorily bind to a heat shock protein, then that immunogen or fragment may be linked to another compound so as to create a heat shock protein-binding domain thereby constructing a hybrid antigen. The heat shock protein-binding domain is selected so that the hybrid peptide will bind in vitro to a heat shock protein such as BiP, hsp70, gp96, or hsp90, alone or in combination with accessory heat shock proteins such as hsp40, or hsp60. Peptides which fulfill this criterion may be identified by panning libraries of antigens known to bind well to one or more heat shock proteins as described in Blond-Elguindi et al., *Cell* 75:717-728 (1993). Using this technique, Blond-Elguindi have concluded that the heat shock protein BiP recognizes polypeptides that contain a heptameric region having the sequence Hy(Trp/X)HyXHyXHy where Hy represents a hydrophobic amino acid residue, particularly tryptophan, leucine or phenylalanine, and X is any amino acid. High affinity heat-shock protein-binding sequences incorporating this motif include:

His Trp Asp Phe Ala Trp Pro Trp [Seq. ID No. 1]; and

Phe Trp Gly Leu Trp Pro Trp Glu [Seq. ID No. 4].

Other heat shock protein binding motifs have also been identified. For example, Auger et al. Nature Medicine 2:306-310 (1996) have identified two pentapeptide binding motifs Gln Lys Arg Ala Ala [SEQ ID No. 5] and
Arg Arg Arg Ala Ala [Seq. ID No. 6]

in HLA-DR types associated with rheumatoid arthritis which bind to heat shock proteins. Heat shock binding motifs have also been identified as consisting of seven to fifteen residue long peptides which are enriched in hydrophobic amino acids. Flynn et al., *Science* 245: 385-390 (1989); Gragerov et al., *J. Molec. Biol.* 235: 848-854 (1994).

The hybrid antigen of the invention incorporates one immunogenic domain and one heat shock protein-binding domain, optionally separated by a short peptide linker. The hybrid peptide of the invention may be synthesized using chemical peptide synthesis methods or it can be synthesized by expression of a nucleic acid construct containing linked sequences encoding the antigenic and heat shock protein-binding domains. One suitable technique utilizes initial separate PCR amplification reactions to produce separate DNA segments encoding the two domains, each with a linker segment attached to one end, followed by fusion of the two amplified products in a further PCR step. This technique is referred to as linker tailing. Suitable restriction sites may also be engineered into regions of interest, after which restriction digestion and ligation is used to produce the desired hybrid peptide-encoding sequence.

Methods of Administration

The heat shock protein/target antigen combinations of the invention may be administered to a subject using either a protein-based or nucleic acid vaccine, so as to produce, in the subject, an amount of heat shock protein/target antigen complex which is effective in inducing a therapeutic immune response in the subject.

The subject may be a human or nonhuman subject.

The term "therapeutic immune response", as used herein, refers to an increase in humoral and/or cellular immunity, as measured by standard techniques, which is directed toward the target antigen. Preferably, but not by way of limitation, the induced level of humoral immunity directed toward target antigen is at least four-fold, and preferably at least 16-fold greater than the levels of the humoral immunity directed toward target antigen prior to the administration of the compositions of this invention to the subject. The immune response may also be measured qualitatively, wherein by means of a suitable in vitro assay or in vivo an arrest in progression or a remission of neoplastic or infectious disease in the subject is considered to indicate the induction of a therapeutic immune response.

Specific amounts of heat shock protein/target antigen administered may depend on numerous factors including the immunogenicity of the particular vaccine composition, the immunocompetence of the subject, the size of the subject and the route of administration. Determining a suitable amount of any given composition for administration is a matter of routine screening.

In specific nonlimiting embodiments of the invention, it may be desirable to include more than one species of heat shock protein, and/or more than one target antigen, in order to optimize the immune response. Such an approach may be particularly advantageous in the treatment of cancer or in the treatment of infections characterized by the rapid development of mutations that result in evasion of the immune response.

In other specific nonlimiting embodiments of the invention, in order to promote binding among members of each heat shock protein/target antigen pair, the ratio of heat shock protein to target antigen may preferably be 1:2 to 1:200. Higher relative levels of antigen are suitable to enhance binding to the heat shock protein.

According to still further specific but nonlimiting embodiments of the invention, the target antigen is not chemically cross-linked to the heat shock protein.

Compositions comprising target antigen/heat shock protein as set forth above are referred to herein as "vaccines". The term vaccine is used to indicate that the compositions of the invention may be used to induce a therapeutic immune response.

A vaccine composition comprising one or more heat shock proteins and one or more target antigens in accordance with the invention may be administered cutaneously, subcutaneously, intravenously, intramuscularly, parenterally, intrapulmonarily, intravaginally, intrarectally, nasally or topically. The vaccine composition may be delivered by injection, particle bombardment, orally or by aerosol.

Incubation of heat shock proteins in solution with the target antigen is sufficient to achieve loading of the antigen onto the heat shock protein in most cases. It may be desirable in some cases, however, to add agents which can assist in the loading of the antigen.

Incubation with heating of the heat shock protein with the target antigen will in general lead to loading of the antigen onto the heat shock protein. In some cases, however, it may be desirable to add additional agents to assist in the loading. For example, hsp40 can facilitate loading of peptides onto hsp70. Minami et al., *Gen. Biol. Chem.* 271: 19617-19624 (1996). Denaturants such as guanidinium HCl or urea can be employed to partially and reversibly destabilize the heat shock protein to make the peptide binding pocket more accessible to the antigen.

Vaccine compositions in accordance with the invention may further include various additional materials, such as a pharmaceutically acceptable carrier. Suitable carriers include any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

The vaccine composition of the invention may also include suitable diluents, preservatives, solubilizers, emulsifiers, adjuvants and/or carriers. Such compositions may be in the form of liquid or lyophilized or otherwise dried formulations and may include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g. glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexing with metal ions, or incorporation of the material into or onto particulate preparations of polymeric compounds such as polylactic acid, polyglycolic acid, hydrogels, etc. or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. The choice of compositions will depend on the physical and chemical properties of the vaccine. For example, a product derived from a membrane-bound form of a protein may require a formulation containing detergent. Controlled or sustained release compositions include formulation in lipophilic depots (e.g. fatty acids, waxes, oils). Also comprehended by the invention are particulate compositions coated with polymers (e.g. poloxamers or poloxamines) and coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhances for various routes of administration, including intramuscular, parenteral, pulmonary, nasal and oral.

As an alternative to direct administration of the heat shock protein and target antigen, one or more polynucleotide constructs may be administered which encode heat shock protein and target antigen in expressible form. The expressible polynucleotide constructs are introduced into cells in the subject using ex vivo or in vivo methods. Suitable methods include injection directly into tissue and tumors, transfecting using liposomes (Fraley et al., *Nature* 370:111-117 (1980)), receptor-mediated endocytosis (Zatloukal, et al., *Ann. NY Acad. Sci.* 660:136-153 (1992)); particle bombardment-mediated gene transfer (Eisenbraun et al., *DNA & Cell Biol.* 12:792-797 (1993)) and transfection using peptide presenting bacteriophage. Barry et al. *Nature Medicine* 2: 299-305 (1996). The polynucleotide vaccine may also be introduced into suitable cells in vitro which are then introduced into the subject.

To construct an expressible polynucleotide, a region encoding the heat shock protein and/or target antigen is prepared as discussed above and inserted into a mammalian expression vector operatively linked to a suitable promoter such as the SV40 promoter, the cytomegalovirus (CMV) promoter or the Rous sarcoma virus (RSV) promoter. The resulting construct may then be used as a vaccine for genetic immunization. The nucleic acid polymer(s) could also be cloned into a viral vector. Suitable vectors include but are not limited to retroviral vectors, adenovirus vectors, vaccinia virus vectors, pox virus vectors and adenovirus-associated vectors. Specific vectors which are suitable for use in the present invention are pCDNA3 (In-Vitrogen), plasmid AHS (which contains the SV40 origin and the adenovirus major late promoter). pRC/CMV (Invitrogen), pCMU II (Paabo et al., *EMBO J.* 5:1921-1927 (1986)), pZip-Neo SV (Cepko et al., Cell 37:1053-1062 (1984)) and pSRα (DNAX, Palo Alto, Calif.).

EXAMPLE 1

Preparation of Hybrid Peptides

Hybrid peptides containing a BiP-binding domain (His-Trp-Asp-Phe-Ala-Trp-Pro-Trp; SEQ ID NO: 1) and an OVA antigenic domain (Ser-Ile-Ile-Asn-Phe-Glu-Lys-Leu; SEQ ID NO:7) separated by a tripeptide linker (gly-ser-gly) were synthesized. Peptides were produced in both orientations, OVA-BiP-binding domain and BiP-binding domain OVA as follows:

Ser-Ile-Ile-Asn-Phe-Glu-Lys-Leu-Gly-Ser-Gly-His-Trp-Asp-Phe-Ala-Trp-Pro-Trp [SEQ ID NO: 8]

and

His-Trp-Asp-Phe-Ala-Trp-Pro-Trp-Gly-Ser-Gly-Ser-Ile-Ile-Asn-Phe-Glu-Lys-Leu [SEQ ID NO: 9].

EXAMPLE 2

Purified mouse cytosolic hsp70 was prepared from *E. coli* DH5α cells transformed with pMS236 encoding mouse cytosolic hsp70. The cells were grown to an optical density (600 nm) of 0.6 at 37° C., and expression was induced by the addition of IPTG to a final concentration of 1 mM. Cells were harvested by centrifugation 2 to 5 hours post induction and the pellets were resuspended to 20 mL with Buffer A (20 mM Hepes pH 7.0, 25 mM KCl, 1 mM DTT, 10 mM $(NH_4)_2SO_4$, 1 mM PMSF). The cells were lysed by passing three times through a French press. The lysate was cleared by a low speed spin, followed by centrifugation at 100,000×G for 30 minutes. The cleared lysate was applied to a Pharmacia XK26 column packed with 100 mL DEAE Sephacel and equilibrated with Buffer A at a flow rate of 0.6 cm/min. The column was washed to stable baseline with Buffer A and eluted with Buffer A adjusted to 175 mM KCl. The eluate was applied to a 25 mL ATP-agarose column (Sigma A2767), washed to baseline with Buffer A, and eluted with Buffer A containing 1 mM MgATP preadjusted to pH 7.0. EDTA was added to the eluate to a final concentration of 2 mM. The eluate which contained essentially pure hsp70 was precipitated by addition of $(NH_4)_2SO_4$ to 80% saturation. The precipitate was resuspended in Buffer A containing 1 mM $MgCl_2$ and dialyzed against the same buffer with multiple changes. The purified hsp70 was frozen in small aliquots at −70° C.

EXAMPLE 3

The purified hsp70 was combined with the synthesized peptides and used for immunization. To form the hsp70/peptide mixtures, approximately 15 ug (21.5 uM) hsp70 was combined with 5 ug of Ova-peptide (0.5 mM, SEQ. ID. NO: 5) or 10 ug (0.5 mM) hybrid peptide (SEQ. ID NOS: 6 and 7) were mixed on ice to a final volume of 10 μl in Buffer B (final concentration: 20 mM Hepes pH 7.0, 150 mM KCl, 10 mM $(NH_4)_2SO_4$, 2 mM $MgCl_2$ and 2 mM MgATP, pH 7.0). The mixtures were incubated for 30 minutes at 37° C. and then used for in vivo immunizations.

C57BL/6 mice were immunized intradermally once a week for a total of two weeks with 10 μL of one of the mixtures described above or with a mixture of TiterMax® (Vaxell, Norcross, Ga.) and Ova-peptide (5 µg). One week after the second immunization, spleen cells were removed and mononuclear cells ($6\text{-}8\times10^7$) were cultured with $3\times10^6$ γ-irradiated (3000 rad) stimulator cells. The stimulator cells were obtained from naive mice that had been sensitized in vitro with Ova-peptide (10 mg/ml) for 30 minutes at room temperature, washed and irradiated at 3000 rads.

Cytotoxicity of spleen cells from vaccinated mice were assayed on Ova-peptide pulsed EL4 cells in an 18-hour chromium release assay. CTL were generated by culturing in vivo immunized spleen cells for 5 days at a concentration of $10^6$ cells/mL in RPMI medium, 10% FCS, penicillin, streptomycin and 2 mM L-glutamine, together with $3\times10^6$ γ-irradiated (3,000 rad) stimulator cells/mL. Target cells were prepared by culturing cells for 1 hour in the presence of 250 µCi of $^{51}$Cr sodium chromate (DuPont, Boston, Mass.) in Tris-phosphate buffer, pH 7.4 at 37° C. for 60 minutes. After washing, $10^4$ $_{51}$Cr-labeled target cells were mixed with effector lymphocytes to yield several different effector/target (E/T) ratios and were incubated for 18 hours. Supernatants were harvested and the radioactivity was measured in a gamma counter. Percent specific lysis was calculated as: 100×[(cpm release by CTL−cpm spontaneous release)/(cpm maximal release−cpm spontaneous release)]. Maximal response was determined by addition of 1% Triton X-100. Spontaneous release of all target in the absence of effector cells was less than 25% of the maximal release.

As shown in FIG. 1, the combination of Hsp70 and the hybrid peptide of either orientation (hsp7+BiP-OVA or hsp70+OVA-BiP) evoked a higher immune response as measured by specific lysis of cells than the hsp70 or TiterMax® adjuvant plus Ova-peptide alone.

EXAMPLE 4

Figure 2:
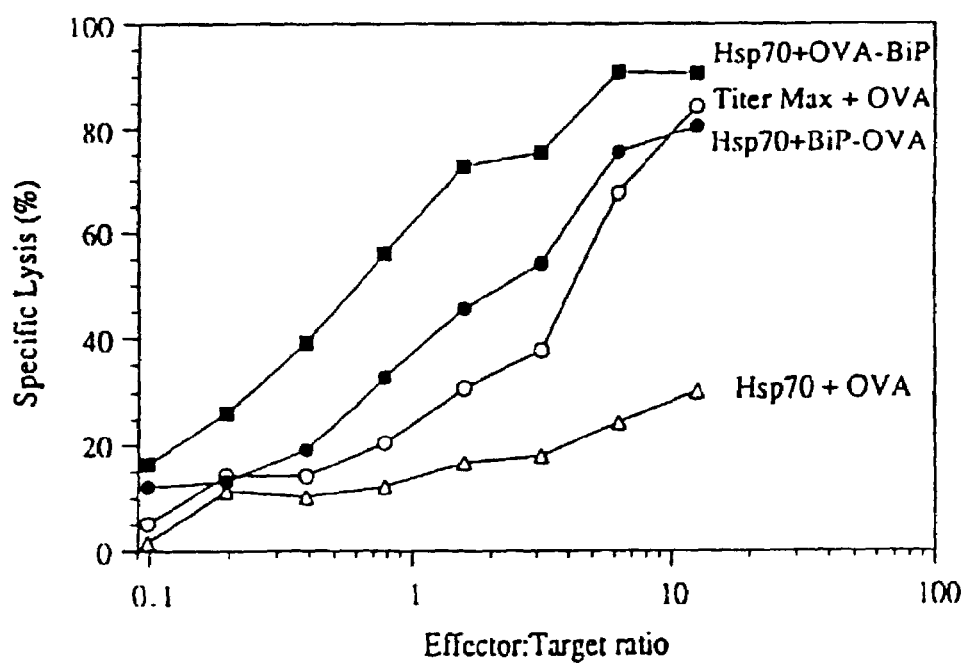
FIG. 2 shows the induction of a cellular immune response using hybrid peptide antigens in accordance with the invention.

The assay of Example 3 was repeated using CTL cell lines which had been maintained by stimulation with irradiated stimulators, syngeneic splenic feeder cells plus T cell growth factors for a period of two weeks. As shown in FIG. 2, the combination of hsp70 and the hybrid peptide of either orientation (hsp70+BiP-OVA or hsp7+OVA-BiP) evoked a higher immune response as measured by specific lysis of cells than the hsp70 or TiterMax® adjuvant plus Ova-peptide alone. Thus, the immune response elicited by the hybrid peptides persisted through additional passages and can be maintained over a period of time.

EXAMPLE 5

Figure 3:
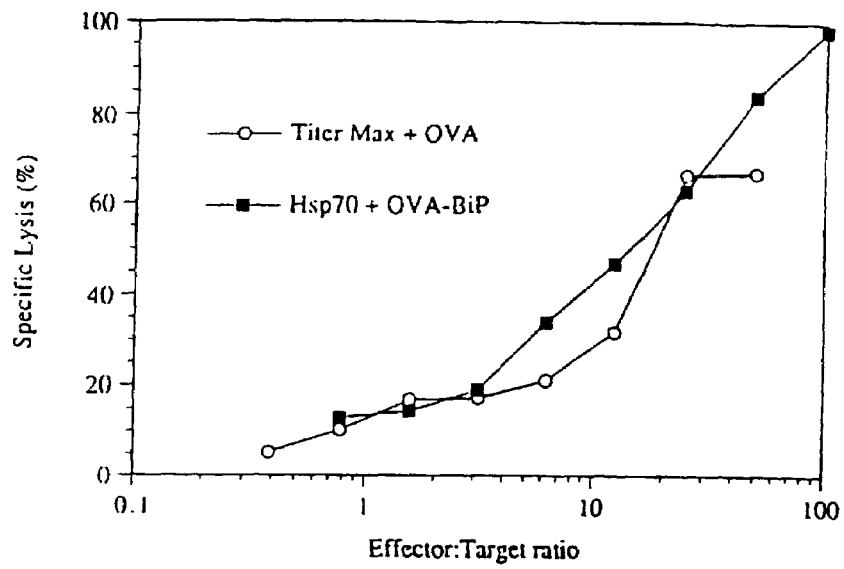
FIG. 3 shows the induction of a cellular immune response using hybrid peptide antigens in accordance with the invention.

The experiment of Example 2 was repeated for the combinations of hsp70 plus BiP-OVA and TiterMax® plus Ova-peptide using only a single immunization one week before removal of the spleen cells. As shown in FIG. 3, the single immunization with either composition was effective in eliciting a cellular immune response.

EXAMPLE 6

Figure 4:
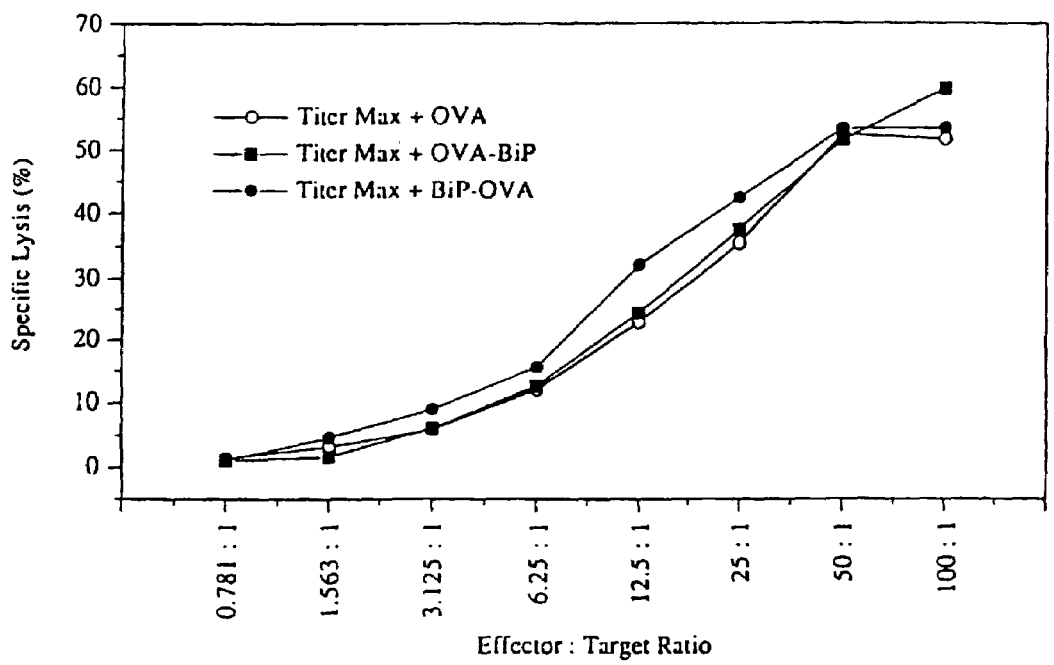
FIG. 4 shows the induction of a cellular immune response using hybrid peptide antigens in accordance with the invention.

The assay of Example 3 was repeated using mixtures of TiterMax® with Ova-peptide or the hybrid peptides of Example 1. As shown in FIG. 4, no significant difference was observed between the Ova-peptide and hybrid peptides demonstrating the specificity of the effect when hybrid peptides are used in association with the heat shock protein.

EXAMPLE 7

Figure 5B:
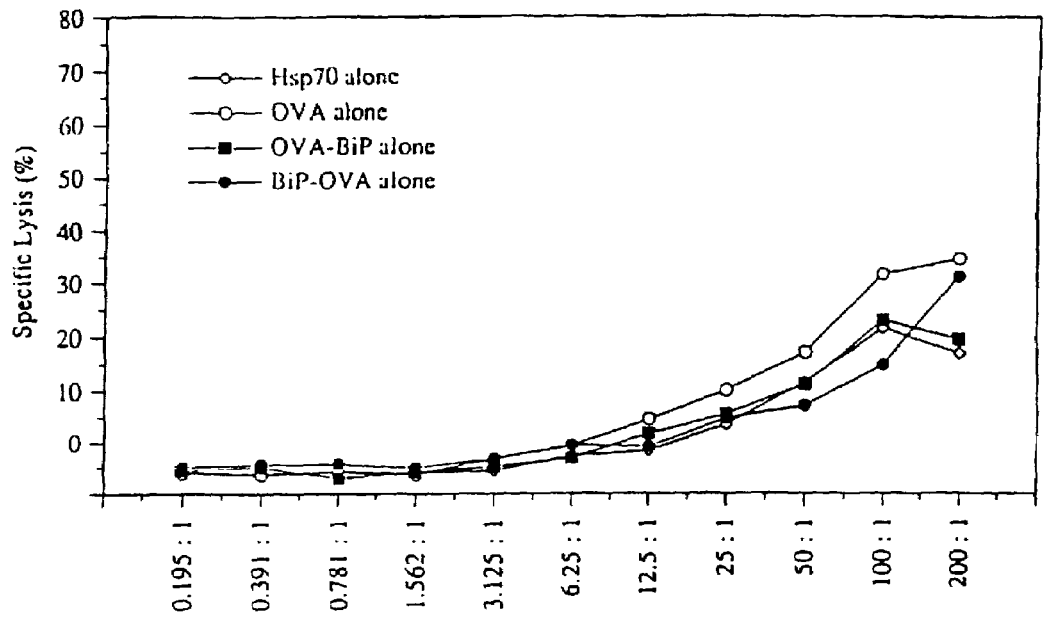
FIGS. 5A and 5B shows the results of control experiments in which hybrid peptide or Ova-peptide and heat shock protein were administered individually to EL4 cells.
Figure 5A:
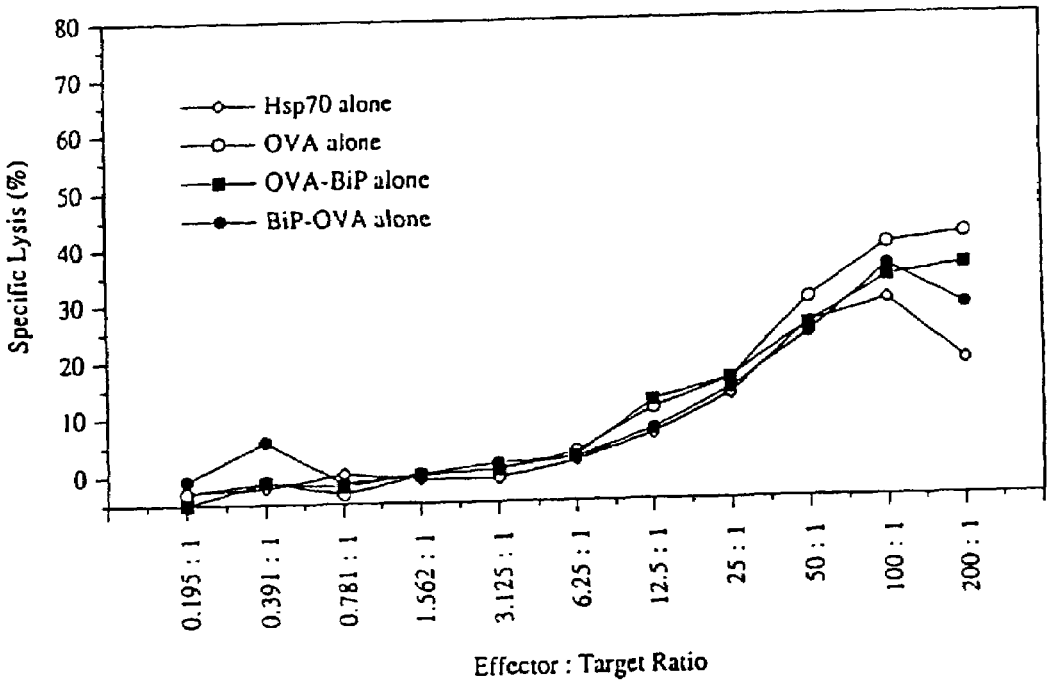

FIGS. 5A and 5B show the results when the procedure of Example 3 was repeated immunizing the mice with hsp70 alone, OVA-peptide alone, Ova-BiP alone or Bip-Ova alone. As shown, the results in all cases were the same when the cells were pulsed with Ova-peptide (FIG. 5A) and when they had not been pulsed. (FIG. 5B). This demonstrates that the response is the result of the combination of the mixture of the antigen (Ova-peptide or hybrid peptide) and the heat shock protein and not to any of the components individually.

EXAMPLE 8

$^{14}$C-labeled OVA-BiP was prepared by alkylation of OVA-BiP with $^{14}$C-formaldehyde. 0.9 mg of OVA-BiP in 300 uL 10% DMSO/water was added to 175 µl of $^{14}$C-formaldehyde (62 µCi) and immediately 50 uL of freshly made up 200 mM NaCNBH$_3$ was added. The reaction was mixed and left at 25° C. for 3 hours. The labeled peptide was repurified by reverse phase HPLC on a C-4 column in a 15 minute 0-100% acetonitrile (0.1% TFA) gradient.

Figure 6:
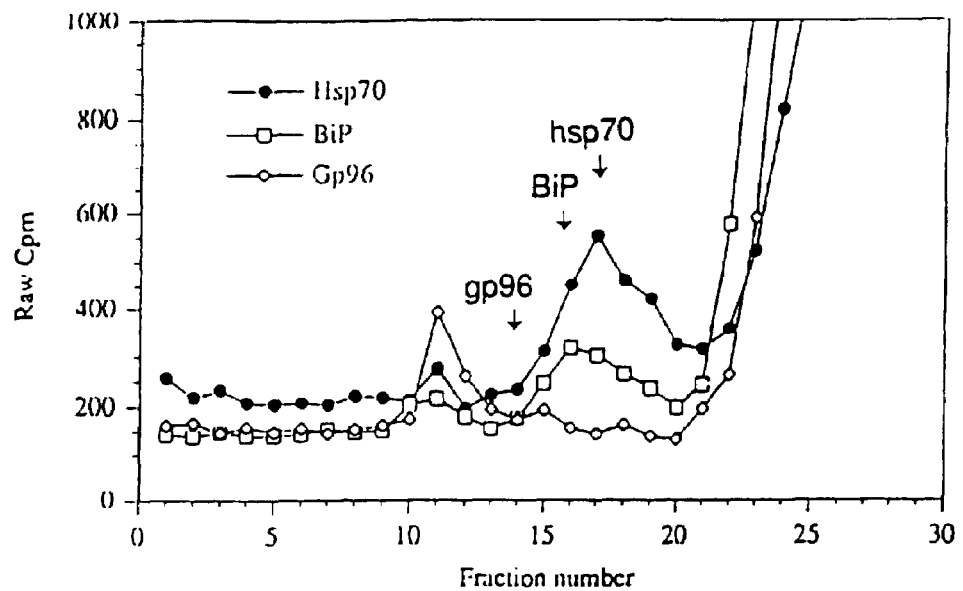
FIG. 6 shows co-elution of hybrid peptides and heat shock proteins from a column, demonstrating binding of the polypeptides to the heat shock protein.

The ability of the OVA-BiP peptide to bind to heat shock proteins was measured by incubating 100 µM (5 µg) $^{14}$C-labeled OVA-BiP with 50 µg of BiP (prepared as in example 11), hsp70 (as prepared in Example 2) or grp96 (prepared as in Example 10) in a final volume of 20 µl of buffer (50 mM Mops, pH 7.2., 200 m mM NaCl, 5 mM MgAcetate) at 37° C. for 30 minutes. The samples were then spun down (5 minutes in a microfuge) and loaded onto a 17 cm long Sephacryl S-300 column equilibrated in binding buffer (50 mM Mops, pH 7.2., 200 mM NaCl, 5 mM MgAcetate) and fractions were collected dropwise. 50 µl of each ~225 µl fraction was counted in scintillation liquid. 10 µl of each fraction was also run on a 12% SDS-PAGE reducing gel. FIG. 6 shows the radioactivity detected in each fraction eluted from the column, together with the center of the peak of heat shock protein as determined by SDS-PAGE. As shown, a significant amount of radioactivity elutes with BiP and hsp70, thus providing evidence that the hybrid peptide binds to these two heat shock proteins. The result for gp96 is unclear because the peak at fraction 11 (which may represent an aggregation phenomenon) and the gp96 peak (fraction 14) elute close together on the column used.

EXAMPLE 9

To prepare $^{125}$I-OVA-BiP, 250 µCi of monoiodinated Bolton-Hunter reagent was transferred into a stoppered vial and the solvent in which it was dissolved was evaporated with a gentle stream of argon gas. To the dried reagent 222 µL of 4.5 mg/mL OVA-BiP in 100 mM NaBO$_3$, pH 8, 9, 10% DMSO was added. The reaction was mixed and incubated at 25° C. for 45 minutes and continued at 4° C. for a further hour. The labeled peptide was repurified by reverse phase HPLC on a C-4 column in a 20 minute, 0-100% acetonitrile (0.1% TFA) gradient.

The iodinated OVA-BiP was combined with BiP in substantially the same manner as the heat shock proteins in Example 7, except that since the iodinated peptide was at a very low concentration, 1 µl (approx 32 ng) of labeled peptide was mixed with 5 µg of unlabeled peptide and this was incubated with 50 µg of BiP in 20 µL of binding buffer. To observe ATP-mediated peptide release, ATP was added to a final concentration of 2 mM after the 30 minute incubation and incubated for a further 5 minutes prior to spinning. These samples were run on the same column as above, but equilibrated in binding buffer supplemented with 2 mM ATP.

Figure 7:
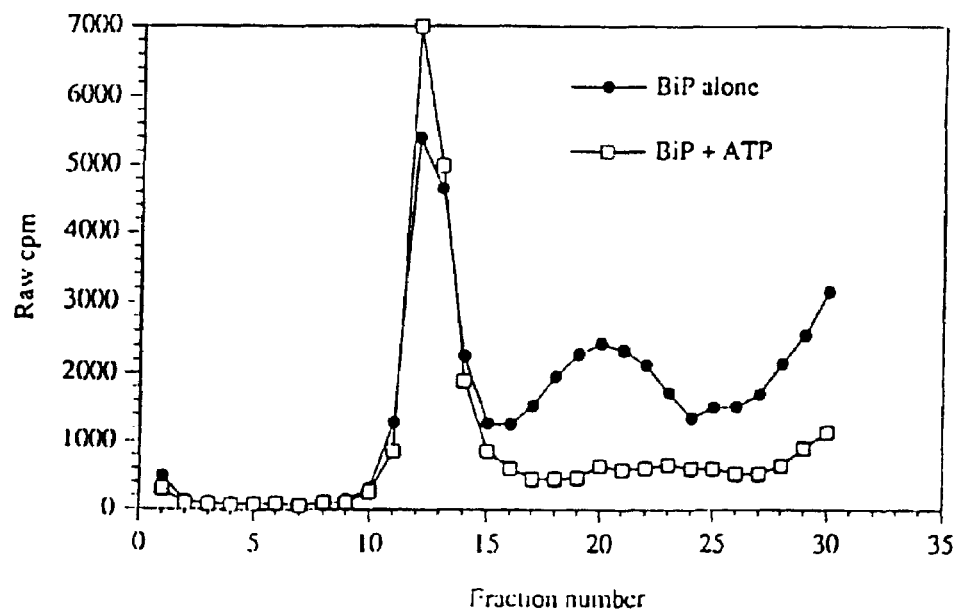
FIG. 7 shows the co-elution of $^{125}$I-OVA-BiP with BiP in the presence and absence of ATP.

FIG. 7 shows the elution profile for a mixture of the $^{125}$I-OVA-BiP and BiP in the presence and absence of 2 mM ATP. As shown, addition of ATP causes the release of the hybrid peptide from the BiP. This is consistent with the observation that ATP mediates release of bound proteins or polypeptides from heat shock proteins.

EXAMPLE 10

Hybrid peptides for use in a vaccine in accordance with the invention against human papilloma virus are prepared using a peptide synthesizer as follows:

E7 (Type 11)-BiP

Leu-Leu-Leu-Gly-Thr-Leu-Asn-Ile-Val-gly-ser-gly-His-Trp-Asp-Phe-Ala-Trp-Pro-Trp [SEQ ID No. 10]

BiP-E7 (Type 11)

His-Trp-Asp-Phe-Ala-Trp-Pro-Trp-gly-ser-gly-Leu-Leu-Leu-Gly-Thr-Leu-Asn-Ile-Val [SEQ ID No. 11]

E7 (Type 16)-BiP

Leu-Leu-Met-Gly-Thr-Leu-Gly-Ile-Val-gly-ser-gly-His-Trp-Asp-Phe-Ala-Trp-Pro-Trp [SEQ ID No. 12]

BiP-E7 (Type 16)

His-Trp-Asp-Phe-Ala-Trp-Pro-Trp-gly-ser-gly-Leu-Leu-Met-Gly-Thr-Leu-Gly-Ile-Val [SEQ ID No. 13]

E7 (TvDe 18)-BiP

Thr-Leu-Gln-Asp-Ile-Val-Leu-His-Leu-gly-ser-gly-His-Trp-Asp-Phe-Ala-Trp-Pro-Trp [SEQ ID No. 14]

BiP-E7 (Type 18)

His-Trp-Asp-Phe-Ala-Trp-Pro-Trp-gly-ser-gly-Thr-Leu-Gln-Asp-Ile-Val-Leu-His-Leu [SEQ ID No. 15]

E7.1 (Type 6b)-BiP

Gly-Leu-His-Cys-Tyr-Glu-Gln-Leu-Val-gly-ser-gly-His-Trp-Asp-Phe-Ala-Trp-Pro-Trp [SEQ ID No. 16]

BiP-E7.1 (Type 6b)

His-Trp-Asp-Phe-Ala-Trp-Pro-Trp-gly-ser-gly-Gly-Leu-His-Cys-Tyr-Glu-Gln-Leu-Val [SEQ ID No. 17]

E7.2 (Type 6b)-BiP

Pro-Leu-Lys-Gln-His-Phe-Gln-Ile-Val-gly-ser-gly-His-Trp-Asp-Phe-Ala-Trp-Pro-Trp [SEQ ID No. 18]

BiP-E7.2 (Type 6b)

His-Trp-Asp-Phe-Ala-Trp-Pro-Trp-gly-ser-gly-Pro-Leu-Lys-Gln-His-Phe-Gln-Ile-Val [SEQ ID No. 19]

Hybrid polypeptides for use in vaccines against human papilloma virus of other types or proteins from other viruses, bacteria etc can be developed by searching their sequences for MHC class I restricted peptide epitopes containing the HLA-A2 peptide binding motif.

EXAMPLE 11

Preparation of Recombinant GP96

The DNA sequence encoding a wild-type or KDEL-deleted gp96 polypeptide was subcloned from pRc/CMV into the vector pET11a (Novagen). Thus upon expression, mature gp96 could be purified from cell lysates.

Vector Construction

PCR amplification of the sequence encoding gp96 (from pRc/CMV) was performed with the following primers. The 5' primer for both wild-type and KDEL-deleted gp96 was complementary to the DNA sequence encoding the amino terminal end of the mature form of gp96 and an Nde I restriction site (CATATG) the ATG of which forms the initiator codon:

5' AGA TAT ACA TAT CCA TGA TGA AGT CCA CGT GG 3'[SEQ ID No. 20]

The 3' primers were complementary to the DNA sequence of gp96 encoding the carboxyl terminal end of the protein, with the nucleotides encoding the KDEL sequence removed in the primer for the KDEL-deleted variant. Both primers contain a BamH I restriction site (GGATCC) followed by a STOP codon as shown:

Wild-Type:

5' TCG GAT CCT TAC AAT TCA TCC TTC TCT GTA GAT TC 3'[SEQ ID No. 21]

KDEL-deleted:

5' TCG GAT CCT TAC TCT GTA GAT TCC TTT TC 3'[SEQ ID No. 22]

The PCR products were cut with Nde I and BamH I and ligated into pET11a (Novagen) which had also been cut with these enzymes. The ligation product was used to transform competent BL21 cells. Clones obtained were screened by expression screening.

Expression and Purification

This procedure is identical for wild-type or KDEL-deleted gp96. Two liters of E. coli BL21 cells transformed with pET11a containing a sequence coding for either wild-type or KDEL-deleted gp96 were grown in 2×TY medium supplemented with 200 ug/ml ampicillin at 37° C. until they reached an absorbance at 600 nm of 0.5-0.6 at which point they were induced by the addition of 1 mM IPTG. The cells were allowed to grow for a further 2-5 hours at 37° C. and then they were harvested by 10 minutes centrifugation at 7000×G. The cell pellet was resuspended in 50 mM Hepes pH 7.5, 50 mM KCl, 5 mM MgAcetate, 20% sucrose, 1 mM PMSF and the cells lysed by passing them through the French Press three times. The cell extract was clarified by a one hour spin at 200000×G and the supernatant retained.

The supernatant was diluted two-fold with cold 50 mM Hepes pH 7.5 and loaded onto a Pharmacia XK26 column containing 50 ml of DE52 anion exchange resin (Whatman) which had been equilibrated in 50 mM Mops pH 7.4., 10 mM NaCl, 5 mM MgAcetate. The bound protein was eluted in a 0-1000 mM NaCl gradient. Fractions containing gp96 were identified by SDS-PAGE and pooled.

The pooled gp96-containing fractions were diluted two-fold with cold 50 mM Mops pH 7.4 and loaded onto a Pharmacia XK16 column containing 15 mL of hydroxylapatite resin (BioRad) which had been washed with 0.5 M $K_2HPO_4$ pH 7.2., 50 mM KCl and equilibrated in 10 mM $K_2HPO_4$, pH 7.2, 50 mM KCl. The bound protein was eluted in a 10-500 mM $K_2HPO_4$ pH 7.2 gradient with the KCl concentration held constant at 50 mM. Fractions containing gp96 were identified by SDS-PAGE and pooled.

The pooled gp96-containing fractions were finally loaded onto a Pharmacia XK26 column containing 25 ml of phenyl Sepharose (Pharmacia) which had been equilibrated in 50 mM Mops pH 7.2, 500 mM NaCl and eluted in a 500-0 mM NaCl gradient. The fractions containing essentially pure gp96 were pooled, concentrated by filtration and made up to 10% glycerol. The purified gp96 was stored frozen at −80° C.

EXAMPLE 12

Construction of BiP Expression Vector and Purification of Recombinant BiP

The DNA sequence encoding the wild-type or KDEL-deleted BiP polypeptide was subcloned from pCDNA3 into the vector pET22 (Novagen), thereby placing it behind and in frame with a DNA sequence that codes for a signal sequence which targets the expressed BiP to the periplasmic space of the bacterial expression host, E. coli. Upon transport into the periplasm the signal sequence is removed and thus mature wild-type or KDEL-deleted BiP can be harvested from the periplasm without any contamination by cytosolic hsp70s.

Vector Construction:

PCR amplification of the sequence encoding BiP (from pCDNA3) was performed with the following primers. The 5' primer for both wild-type and KDEL-deleted BiP was complementary to the DNA sequence of BiP encoding the amino terminal end of the mature form of BiP with an Msc I restriction site (TGGCCA) immediately upstream from the initiator ATG codon:

5' AGA TAT GTG GCC ATG GAG GAG GAG GAC AAG 3'[SEQ ID No. 23]

The 3 primers were complementary to the DNA sequence of BiP encoding the carboxyl terminal end of the protein, with the nucleotides encoding the KDEL sequence removed in the primer for the KDEL-deleted variant. Both primers contain a BamH I restriction site (GGATCC) followed by stop codon as shown:

Wild-Type:

5' TCG GAT CCC TAC AAC TCA TCT TTT TCT G 3'[SEQ ID No. 24]

KDEL-deleted:

5' TCG GAT CCC TAT TCT GAT GTA TCC TCT TCA CC 3'[SEQ ID No. 25]

The PCR products were cut with Msc I and BamH I and ligated into pET22 (Novagen) which had also been cut with these enzymes. The ligation product was used to transform competent BL21 cells. Clones obtained were screened by expression screening.

Expression and Purification

The procedure is identical for wild-type or KDEL-deleted BiP. Two liters of BL21 cells transformed with pET22 containing a sequence coding for either wild-type or KDEL deleted BiP were grown in 2×TY medium supplemented with 200 μg/ml ampicillin at 37° C. until they reached an absorbance at 600 nm of 0.5-0.6 at which point they were induced by the addition of 1 mM IPTG. The cells were allowed to grow for a further 2-5 hours at 37° C. and then they were harvested by 10 minutes centrifugation at 7000×G. The cell pellet was gently resuspended in 400 mL (or 80 mL/gm cells) of 30 mM Tris pH 8.0, 20% Sucrose, 1 mM PMSF. Following resuspension of the cells EDTA was added to 1 mM and the suspension incubated at room temperature for 5 minutes. The cells were then spun down for 15 minutes at 7000×G and resuspended in 400 mL of ice cold 5 mM MgSO$_4$, 1 mM PMSF and incubated at 4° C. for 10 minutes. The cells were then spun down once again and the supernatant kept since this now constitutes the periplasmic extract.

The periplasmic extract was loaded onto a Pharmacia XK26 column containing 25 mL of DE52 anion exchange resin (Whatman) which had been equilibrated in 50 mM Mops pH 7.4, 10 mM NaCl. The bound protein was eluted in a 10-500 mM NaCl gradient. Fractions containing eluted BiP were identified by SDS-PAGE and pooled. The pooled BiP was subsequently run onto a Pharmacia XK26 column containing 10 mL of ATP agarose which had been equilibrated in 50 mM Mops pH 7.4., 100 mM NaCl, 5 mM MgAcetate, 10 mM KCl. After loading the pooled BiP containing fractions the column was washed until the baseline of absorption at 280 nm reached zero. Finally the bound BiP was eluted with the same buffer supplemented with 1 mM ATP. The eluate was concentrated by filtration, made up to 10% glycerol and stored frozen at −80° C.

EXAMPLE 13

Preparation of Recombinant Mouse HSP40 Plasmid Constructions

The DNA fragment used to introduce an Nde I site at the initiation methionine of hsp40 was constructed via polymerase chain reaction (PCR) using an Nde-primer 5'-CCGCAGGAGGGGCATATGGGTAAAGAC-3' [SEQ ID No. 26]

and an Nco-primer

5'-GAGGGTCTCCATGGAATGTGTAGCTG-3' [SEQ ID No. 27].

The latter included an Nco I site corresponding to nucleotide 322 of the human hsp40 cDNA clone, pBSII-hsp40, Ohtsuka, K., *Biochem. Biophys. Res. Commun.* 197: 235-240 (1991), which was used as the template. The Hsp40-coding region of pBSII-hsp40 was digested with BamH I and Sac I and inserted into the complementary sites in a modified form of the plasmid pET-3a (Novagen, Inc.). The PCR-amplified DNA was digested with Nde I and Nco I, and replaced the Nde I-Nco I region of the above plasmid to create the plasmid pET/hsp40, expressing hsp40.

Protein Purification:

To purify recombinant human hsp40, the plasmid pET/hsp40 was transformed into BL21(DE3) cells grown at 37° C. After a 2 hour incubation with 0.4 mM isopropyl thio-b-D-galactoside (IPTG), cells were lysed in a French Pressure Cell (SLM Instruments, Inc.) in buffer A [20 mM Tris-HCl, pH 7.5, 20 mM NaCl, 1 mM EDTA] containing 1 mM PMSF. The cleared lysate was mixed with DEAE-Sephacel (Pharmacia) on ice for 1 h. The unbound material was collected and the resin was washed with buffer A. The flow-through and first wash were combined and loaded onto a hydroxyapatite HTP column (Bio-Rad) equilibrated with 100 mM potassium phosphate, pH 7.6. The column was washed with the same buffer and Hsp40 was eluted with a linear gradient of 100-300 mM potassium phosphate, pH 7.6. Peak fractions were rechromatographed on an HTP column after passing them through a DEAE-Sephacel column.

EXAMPLE 14

Vaccine compositions were prepared by combining recombinant mouse hsp70 (prepared as in example 2), recombinant human hsp40 (prepared as in example 13) and Ova-peptide Ser-Ile-Ile-Asn-Phe-Glu-Lys-Leu [SEQ ID No. 7] in a final volume of 10 µl of buffer (20 mM Hepes pH 7.0, 150 mM KCl, 10 mM $(NH_4)_2SO_4$, 2 mM $MgCl_2$ and 2 mM MgATP) as follows:

| Sample | hsp70 | hsp40 | ova |
| --- | --- | --- | --- |
| OVA-alone | nil | nil | 5 ug |
| Hsp70/40 | 15 ug | 8 ug | nil |
| Hsp70/40 + OVA | 15 ug | 8 ug | 5 ug |
| Hsp70 + OVA | 15 ug | | 5 ug |

The mixtures were incubated for 30 minutes at 37° C. prior to use for immunizations.

C57BL/6 mice were immunized intradermally once a week for a total of two weeks with 10 uL of one of the mixtures described above or with a mixture of TiterMax® (Vaxcell, Norcross, Ga.) and Ova-peptide (5 ug). One week after the second immunization, spleen cells were removed and mononuclear cells ($6-8\times10^7$) were cultured with $3\times10^6$ γ-irradiated (3000 rad) stimulator cells. The stimulator cells were obtained from naive mice that had been sensitized in vitro with ova peptide (10 mg/ml) for 30 minutes at room temperature, washed and irradiated at 3000 rads.

Cytotoxicity of spleen cells from vaccinated mice was assayed on Ova-peptide pulsed EL4 cells in an 18-hour chromium release assay. CTL were generated by culturing in vivo immunized spleen cells for 5 days at a concentration of $10^6$ cells/mL in RPMI medium, 10% FCS, penicillin, streptomycin and 2 mM L-glutamine, together with $3\times10^6$ γ-irradiated (3,000 rad) stimulator cells/mL. Target cells were prepared by culturing cells for 1 hour in the presence of 250 uCi of $^{51}$Cr sodium chromate (DuPont, Boston, Mass.) in Tris-phosphate buffer, pH 7.4 at 37° C. for 60 minutes. After washing, $10^4$ $^{51}$Cr-labeled target cells were mixed with effector lymphocytes to yield several different effector/target (E/T) ratio and were incubated for 18 hours. Supernatants were harvested and the radioactivity was measured in a gamma counter. Percent specific lysis was calculated as: 100×[Cpm release by CTL−cpm spontaneous release)/(cpm maximal release−cpm spontaneous release)]. Maximal response was determined by addition of 1% Triton X-100. Spontaneous release of all target in the absence of effector cells was less than 25% of the maximal release.

Figure 8:
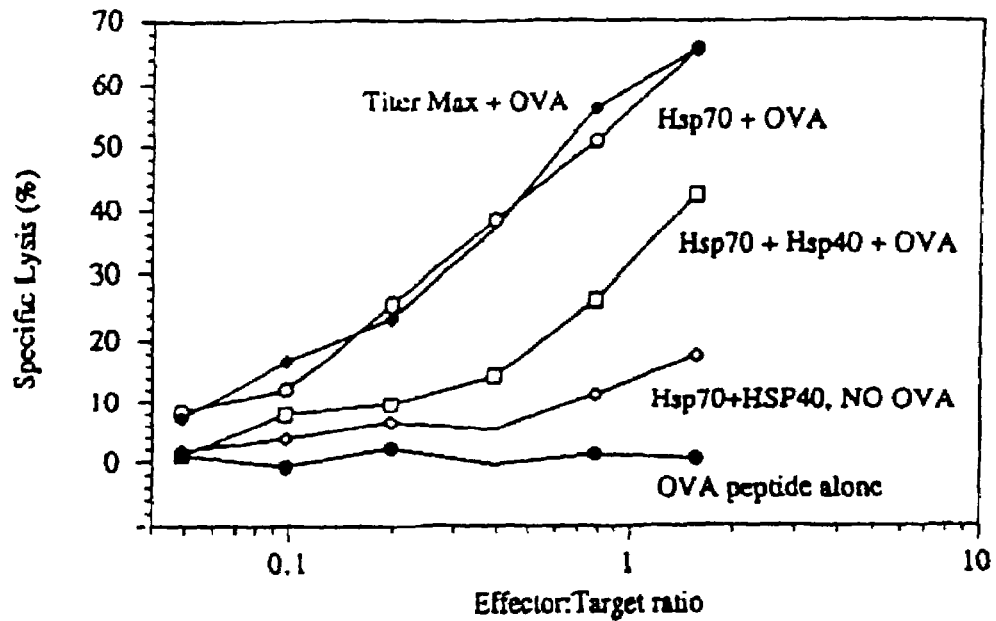
FIG. 8 shows the killing efficacy of T-cells primed with various combinations of antigens and heat shock proteins on EL4 cells pulsed with antigen.

The results of this study are shown in FIG. 8. As shown, combinations of antigen with hsp70 or a mixture of hsp70 and hsp40 are effective to produce a CTL response to the antigen, while the administration of the antigen alone or a combination of heat shock proteins is not.

EXAMPLE 15

Figure 9:
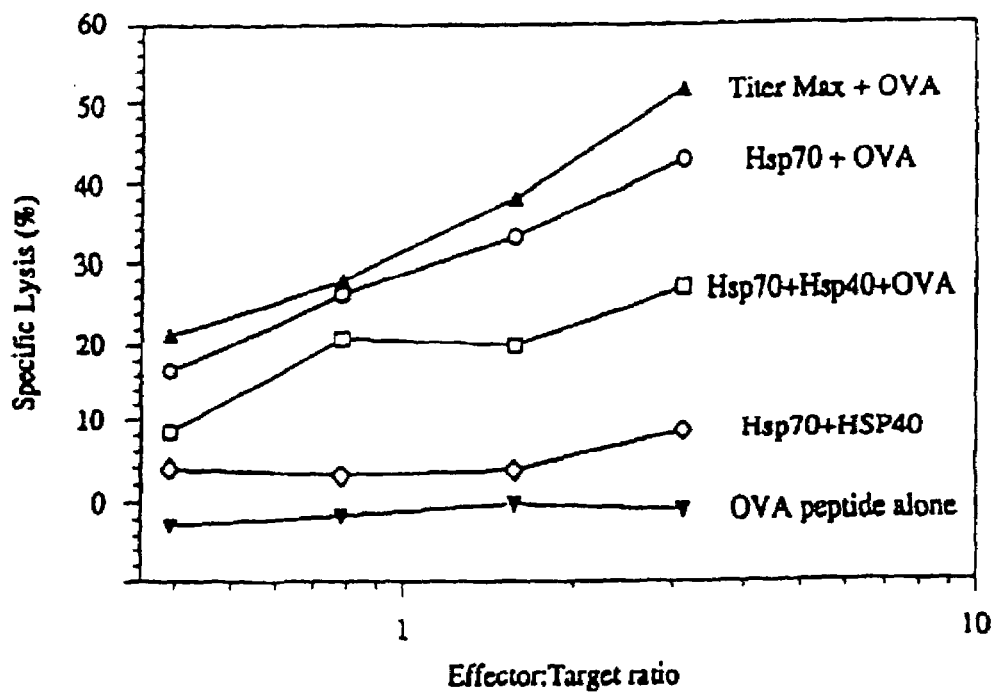
FIG. 9 shows the killing efficacy of T-cells primed with various concentrations of antigens and heat shock proteins on EG7 lymphoma cells.

The experiment of Example 14 was repeated using EG7 lymphoma cells, Moore et al., *Cell* 54: 777-785 (1988), in place of the EL4 cells. The results are shown in FIG. 9 and are comparable to those observed using EL4 cells.

Various publications are cited herein, the contents of which are hereby incorporated by reference in their entireties.

---

The invention claimed is:

1. A composition comprising
  (a) isolated complexes each comprising a hybrid antigen non-covalently bound to a heat shock protein, wherein the hybrid antigen comprises an immunogenic domain and a heat shock protein binding domain, wherein the immunogenic domain is covalently linked to the heat shock protein binding domain; wherein the heat shock protein binding domain is a peptide, and wherein the immunogenic domain comprises an epitope of an antigen of: a neoplastic disease, an infectious agent of an infectious disease, an autoimmune disease or an allergy; and
  (b) a pharmaceutically acceptable carrier.

2. The composition of claim 1, wherein said immunogenic domain comprises a protein or peptide antigen, or a selected epitope of said protein or peptide antigen.

3. The composition of claim 2, wherein said immunogenic domain is 7-20 amino acids.

4. The composition of claim 2, wherein said immunogenic domain is 4-100 amino acids.

5. The composition of claim 1 or 2, wherein said immunogenic domain comprises an epitope associated with the activation of B cells, T helper cells or cytotoxic T cells.

6. The composition of claim 1, wherein said immunogenic domain comprises a carbohydrate, a nucleic acid or a lipid.

7. The composition of claim 1, wherein the heat shock protein is prepared using recombinant techniques.

8. The composition of claim 1, 2 or 4, wherein said heat shock protein binding domain is 7-15 amino acids.

9. The composition of claim 5, wherein said heat shock protein binding domain is 7-15 amino acids.

10. The composition of claim 1, wherein the heat shock protein is selected from the group consisting of BiP, hsp70, hsc70, gp96, hsp60, hsp40 and hsp90.

11. The composition of claim 1, wherein the heat shock protein is hsp70.

12. The composition of claim 1, wherein the heat shock protein is hsc 70.

13. The composition of claim 1, wherein the heat shock protein is gp96.

14. The composition of claim 1, wherein the heat shock protein is BiP.

15. The composition of claim 1, wherein said heat shock protein binding domain comprises the amino acid sequence His Trp Asp Phe Ala Trp Pro Trp (SEQ ID NO:1).

16. The composition of claim 1, wherein said heat shock protein binding domain comprises the amino acid sequence Phe Trp Gly Leu Trp Pro Trp Glu (SEQ ID NO:4), Gln Lys Arg Ala Ala (SEQ ID NO:5) or Arg Arg Arg Ala Ala (SEQ ID NO:6).

17. The composition of claim 1, wherein said immunogenic domain and said heat shock protein binding domain are separated by a peptide linker.

18. The composition of claim 17, wherein the peptide linker is Gly Ser Gly.

19. The composition of claim 1, wherein the hybrid antigen is a peptide.

20. The composition of claim 1, wherein the isolated complexes comprise different heat shock proteins.

21. The composition of claim 1, 4, 10, or 11, wherein the isolated complexes comprise different hybrid antigens.

22. The composition of claim 1, wherein the immunogenic domain comprises an epitope of an antigen of a neoplastic disease, or an epitope of an antigen of an infectious agent of an infectious disease.

23. The composition of claim 21, wherein the immunogenic domain comprises an epitope of an antigen of a neoplastic disease, or an epitope of an antigen of an infectious agent of an infectious disease.

24. The composition of claim 1, wherein the immunogenic domain comprises an epitope of an antigen of an autoimmune disease or allergy.

25. The composition of claim 22, wherein the immunogenic domain comprises an epitope of an antigen of a neoplastic disease.

26. The composition of claim 25, wherein the neoplastic disease is selected from the group consisting of a sarcoma, lymphoma, leukemia and carcinoma.

27. The composition of claim 26, wherein the neoplastic disease is selected from the group consisting of melanoma, carcinoma of the breast, carcinoma of the prostate, ovarian carcinoma, carcinoma of the cervix, uterine carcinoma, colon carcinoma, carcinoma of the lung, glioblastoma, and astrocytoma.

28. The composition of claim 22, wherein the immunogenic domain comprises an epitope of an antigen of an infectious agent of an infectious disease.

29. The composition of claim 28, wherein the infectious agent is a bacterium, virus, protozoan, mycoplasma, fungus, yeast, parasite or prion.

30. The composition of claim 28, wherein the infectious agent is a bacterium.

31. The composition of claim 28, wherein the infectious agent is a virus.

32. The composition of claim 28, wherein the infectious agent is a protozoan.

33. The composition of claim 30, wherein the bacterium is selected from the group consisting of *Salmonella, Staphylococcus, Streptococcus, Enterococcus, Clostridium, Escherichia, Klebsiella, Vibrio, Mycobacterium*, and *Mycoplasma pneumoniae*.

34. The composition of claim 31, wherein the virus is selected from the group consisting of a human papilloma virus, herpes virus, retrovirus, hepatitis virus, influenza virus, rhinovirus, respiratory syncytial virus, cytomegalovirus, adenovirus, herpes simplex virus, herpes zoster virus, human immunodeficiency virus 1, and human immunodeficiency virus 2.

35. The composition of claim 32, wherein the protozoan is selected from the group consisting of an amoeba, a malarial parasite, and *Trypanosoma cruzi*.

36. The composition of claim 1, 4, 10 or 22, wherein the heat shock protein is a human heat shock protein.

37. The composition of claim 21, wherein the heat shock protein is a human heat shock protein.

38. The composition of claim 1, 4, 10 or 22 further comprising one or more adjuvants.

39. The composition of claim 21 further comprising one or more adjuvants.

40. A method for inducing an immune response to an immunogenic domain in a subject in need thereof, comprising administering, to the subject, the composition of any one of claims 1, 4, 10, or 22, whereby an immune response to said immunogenic domain is induced.

41. A method for inducing an immune response to an immunogenic domain in a subject in need thereof, comprising administering, to the subject, the composition of claim 21, whereby an immune response to said immunogenic domain is induced.

42. A method for treating an infectious disease in a subject in need thereof, comprising administering, to the subject, a therapeutically effective amount of the composition of claim 28.

43. A method for treating a neoplastic disease in a subject in need thereof, comprising administering, to the subject, a therapeutically effective amount of the composition of claim 25.

44. A method for treating a neoplastic disease in a subject in need thereof, comprising administering, to the subject, a therapeutically effective amount of the composition of claim 23, and wherein said immunogenic domain comprises an antigen of said neoplastic disease.

45. The method of claim 40, wherein said administering is repeated at least once.

46. The method of claim 42 or 43 wherein said administering is repeated at least once.

47. The method of claim 40, wherein said subject is a human.

48. The method of claim 42 or 43 wherein said subject is a human.

* * * * *

SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
      (A) LENGTH: 8
      (B) TYPE: amino acid
      (C) STRANDEDNESS: <Unknown>
      (D) TOPOLOGY: linear (ii) MOLECULE TYPE: peptide (iii) HYPOTHETICAL: no (v) FRAGMENT TYPE: internal (vi) ORIGINAL SOURCE:
      (A) ORGANISM: mouse (ix) FEATURE:
      (D) OTHER INFORMATION: heat shock binding sequence (xi) SEQUENCE DESCRIPTION: SEQ ID NO: 1:

His Trp Asp Phe Ala Trp Pro Trp
            5

(2) INFORMATION FOR SEQ ID NO: 2:

```
      (i) SEQUENCE CHARACTERISTICS:
          (A) LENGTH: 9
          (B) TYPE: amino acid
          (C) STRANDEDNESS: <Unknown>
          (D) TOPOLOGY: linear (ii) MOLECULE TYPE: peptide (iii) HYPOTHETICAL: no (v) FRAGMENT TYPE: internal (vi) ORIGINAL SOURCE:
          (A) ORGANISM: human (ix) FEATURE:
          (D) OTHER INFORMATION: position 2 is Leu or Met; position 6 is
              Val, Ile, Leu or Thr; position 9 is Val or Leu.
          (D) OTHER INFORMATION: HLA-A2 peptide binding motif (xi) SEQUENCE DESCRIPTION: SEQ ID NO: 2:

Xaa Xaa Xaa Xaa Xaa Xaa Xaa Xaa Xaa
                5

(2) INFORMATION FOR SEQ ID NO: 3:

(i) SEQUENCE CHARACTERISTICS:
          (A) LENGTH: 9
          (B) TYPE: amino acid
          (C) STRANDEDNESS: <Unknown>
          (D) TOPOLOGY: linear (ii) MOLECULE TYPE: peptide (iii) HYPOTHETICAL: no (v) FRAGMENT TYPE: internal (vi) ORIGINAL SOURCE:
          (A) ORGANISM: human (ix) FEATURE:
          (D) OTHER INFORMATION: HLA-A2 peptide binding motif (xi) SEQUENCE DESCRIPTION: SEQ ID NO: 3:

Xaa Xaa Xaa Xaa Xaa Xaa Xaa Xaa Val
                5

(2) INFORMATION FOR SEQ ID NO: 4:

(i) SEQUENCE CHARACTERISTICS:
          (A) LENGTH: 8
          (B) TYPE: amino acid
          (C) STRANDEDNESS: <Unknown>
          (D) TOPOLOGY: linear (ii) MOLECULE TYPE: peptide (iii) HYPOTHETICAL: no (v) FRAGMENT TYPE: internal (vi) ORIGINAL SOURCE:
          (A) ORGANISM: <Unknown>

(ix) FEATURE:
          (D) OTHER INFORMATION:heat shock protein binding motif (xi) SEQUENCE DESCRIPTION: SEQ ID NO: 4:

Phe Trp Gly Leu Trp Pro Trp Glu
                5

(2) INFORMATION FOR SEQ ID NO: 5:
```

```
    (i) SEQUENCE CHARACTERISTICS:
        (A) LENGTH: 5
        (B) TYPE: amino acid
        (C) STRANDEDNESS: <Unknown>
        (D) TOPOLOGY: linear (ii) MOLECULE TYPE: peptide (iii) HYPOTHETICAL: no (v) FRAGMENT TYPE: internal (vi) ORIGINAL SOURCE:
        (A) ORGANISM: human (ix) FEATURE:
        (D) OTHER INFORMATION: HLA-DR peptide binding motif (xi) SEQUENCE DESCRIPTION: SEQ ID NO: 5:

Gln Lys Arg Ala Ala
                5

(2) INFORMATION FOR SEQ ID NO: 6:

(i) SEQUENCE CHARACTERISTICS:
        (A) LENGTH: 5
        (B) TYPE: amino acid
        (C) STRANDEDNESS: <Unknown>
        (D) TOPOLOGY: linear (ii) MOLECULE TYPE: peptide (iii) HYPOTHETICAL: no (v) FRAGMENT TYPE: internal (vi) ORIGINAL SOURCE:
        (A) ORGANISM: human (ix) FEATURE:
        (D) OTHER INFORMATION: HLA-DR peptide binding motif (xi) SEQUENCE DESCRIPTION: SEQ ID NO: 6:

Arg Arg Arg Ala Ala
                5

(2) INFORMATION FOR SEQ ID NO: 7:

(i) SEQUENCE CHARACTERISTICS:
        (A) LENGTH: 8
        (B) TYPE: amino acid
        (C) STRANDEDNESS: <Unknown>
        (D) TOPOLOGY: linear (ii) MOLECULE TYPE: peptide (iii) HYPOTHETICAL: no (v) FRAGMENT TYPE: internal (vi) ORIGINAL SOURCE:
        (A) ORGANISM: chicken (ix) FEATURE:
        (D) OTHER INFORMATION: OVA-peptide (xi) SEQUENCE DESCRIPTION: SEQ ID NO: 7:

Ser Ile Ile Asn Phe Glu Lys Leu
                5

(2) INFORMATION FOR SEQ ID NO: 8:
```

(i) SEQUENCE CHARACTERISTICS:
            (A) LENGTH: 19
            (B) TYPE: amino acid
            (C) STRANDEDNESS: <Unknown>
            (D) TOPOLOGY: linear (ii) MOLECULE TYPE: peptide (iii) HYPOTHETICAL: no (v) FRAGMENT TYPE: internal (vi) ORIGINAL SOURCE:
            (A) ORGANISM: <Unknown>

(ix) FEATURE:
            (D) OTHER INFORMATION:

(xi) SEQUENCE DESCRIPTION: SEQ ID NO: 8:

Ser Ile Ile Asn Phe Glu Lys Leu Gly Ser Gly His
                  5                   10

Trp Asp Phe Ala Trp Pro Trp
        15

(2) INFORMATION FOR SEQ ID NO: 9:

(i) SEQUENCE CHARACTERISTICS:
            (A) LENGTH: 19
            (B) TYPE: amino acid
            (C) STRANDEDNESS: <Unknown>
            (D) TOPOLOGY: linear (ii) MOLECULE TYPE: peptide (iii) HYPOTHETICAL: no (v) FRAGMENT TYPE: internal (vi) ORIGINAL SOURCE:
            (A) ORGANISM: <Unknown>

(ix) FEATURE:
            (D) OTHER INFORMATION:

(xi) SEQUENCE DESCRIPTION: SEQ ID NO: 9:

His Trp Asp Phe Ala Trp Pro Trp Gly Ser Gly Ser
                  5                   10

Ile Ile Asn Phe Glu Lys Leu
        15

(2) INFORMATION FOR SEQ ID NO: 10:

(i) SEQUENCE CHARACTERISTICS:
            (A) LENGTH: 20
            (B) TYPE: amino acid
            (C) STRANDEDNESS: <Unknown>
            (D) TOPOLOGY: linear (ii) MOLECULE TYPE: peptide (iii) HYPOTHETICAL: yes (v) FRAGMENT TYPE: internal (vi) ORIGINAL SOURCE:
            (A) ORGANISM: <Unknown>

(ix) FEATURE:
            (D) OTHER INFORMATION:hybrid peptide for human papilloma
                virus vaccine (xi) SEQUENCE DESCRIPTION: SEQ ID NO: 10:

```
Leu Leu Leu Gly Thr Leu Asn Ile Val Gly Ser Gly
                5                   10

His Trp Asp Phe Ala Trp Pro Trp
           15                  20

(2) INFORMATION FOR SEQ ID NO: 11:

(i) SEQUENCE CHARACTERISTICS:
        (A) LENGTH: 20
        (B) TYPE: amino acid
        (C) STRANDEDNESS: <Unknown>
        (D) TOPOLOGY: linear (ii) MOLECULE TYPE: peptide (iii) HYPOTHETICAL: yes (v) FRAGMENT TYPE: internal (vi) ORIGINAL SOURCE:
        (A) ORGANISM: <Unknown>

(ix) FEATURE:
        (D) OTHER INFORMATION:hybrid peptide for human papilloma
            virus vaccine (xi) SEQUENCE DESCRIPTION: SEQ ID NO: 11:

His Trp Asp Phe Ala Trp Pro Trp Gly Ser Gly Leu
                5                   10

Leu Leu Gly Thr Leu Asn Ile Val
           15                  20

(2) INFORMATION FOR SEQ ID NO: 12:

(i) SEQUENCE CHARACTERISTICS:
        (A) LENGTH: 20
        (B) TYPE: amino acid
        (C) STRANDEDNESS: <Unknown>
        (D) TOPOLOGY: linear (ii) MOLECULE TYPE: peptide (iii) HYPOTHETICAL: yes (v) FRAGMENT TYPE: internal (vi) ORIGINAL SOURCE:
        (A) ORGANISM: <Unknown>

(ix) FEATURE:
        (D) OTHER INFORMATION:hybrid peptide for human papilloma
            virus vaccine (xi) SEQUENCE DESCRIPTION: SEQ ID NO: 12:

Leu Leu Met Gly Thr Leu Gly Ile Val Gly Ser Gly
                5                   10

His Trp Asp Phe Ala Trp Pro Trp
           15                  20

(2) INFORMATION FOR SEQ ID NO: 13:

(i) SEQUENCE CHARACTERISTICS:
        (A) LENGTH: 20
        (B) TYPE: amino acid
        (C) STRANDEDNESS: <Unknown>
        (D) TOPOLOGY: linear (ii) MOLECULE TYPE: peptide (iii) HYPOTHETICAL: yes
```

(v) FRAGMENT TYPE: internal (vi) ORIGINAL SOURCE:
            (A) ORGANISM: <Unknown>

(ix) FEATURE:
            (D) OTHER INFORMATION:hybrid peptide for human papilloma
                virus vaccine (xi) SEQUENCE DESCRIPTION: SEQ ID NO: 13:

His Trp Asp Phe Ala Trp Pro Trp Gly Ser Gly Leu
                  5                  10

Leu Met Gly Thr Leu Gly Ile Val
          15                  20

(2) INFORMATION FOR SEQ ID NO: 14:

(i) SEQUENCE CHARACTERISTICS:
            (A) LENGTH: 20
            (B) TYPE: amino acid
            (C) STRANDEDNESS: <Unknown>
            (D) TOPOLOGY: linear (ii) MOLECULE TYPE: peptide (iii) HYPOTHETICAL: yes (v) FRAGMENT TYPE: internal (vi) ORIGINAL SOURCE:
            (A) ORGANISM: <Unknown>

(ix) FEATURE:
            (D) OTHER INFORMATION:hybrid peptide for human papilloma
                virus vaccine (xi) SEQUENCE DESCRIPTION: SEQ ID NO: 14:

Thr Leu Gln Asp Ile Val Leu His Leu Gly Ser Gly
                  5                  10

His Trp Asp Phe Ala Trp Pro Trp
          15                  20

(2) INFORMATION FOR SEQ ID NO: 15:

(i) SEQUENCE CHARACTERISTICS:
            (A) LENGTH: 20
            (B) TYPE: amino acid
            (C) STRANDEDNESS: <Unknown>
            (D) TOPOLOGY: linear (ii) MOLECULE TYPE: peptide (iii) HYPOTHETICAL: yes (v) FRAGMENT TYPE: internal (vi) ORIGINAL SOURCE:
            (A) ORGANISM: <Unknown>

(ix) FEATURE:
            (D) OTHER INFORMATION:hybrid peptide for human papilloma
                virus vaccine (xi) SEQUENCE DESCRIPTION: SEQ ID NO: 15:

His Trp Asp Phe Ala Trp Pro Trp Gly Ser Gly Thr
                  5                  10

Leu Gln Asp Ile Val Leu His Leu
          15                  20

(2) INFORMATION FOR SEQ ID NO: 16:

```
    (i) SEQUENCE CHARACTERISTICS:
        (A) LENGTH: 20
        (B) TYPE: amino acid
        (C) STRANDEDNESS: <Unknown>
        (D) TOPOLOGY: linear (ii) MOLECULE TYPE: peptide (iii) HYPOTHETICAL: yes (v) FRAGMENT TYPE: internal (vi) ORIGINAL SOURCE:
        (A) ORGANISM: <Unknown>

(ix) FEATURE:
        (D) OTHER INFORMATION:hybrid peptide for human papilloma
            virus vaccine (xi) SEQUENCE DESCRIPTION: SEQ ID NO: 16:

Gly Leu His Cys Tyr Glu Gln Leu Val Gly Ser Gly
                5                  10

His Trp Asp Phe Ala Trp Pro Trp
          15                  20

(2) INFORMATION FOR SEQ ID NO: 17:

(i) SEQUENCE CHARACTERISTICS:
        (A) LENGTH: 20
        (B) TYPE: amino acid
        (C) STRANDEDNESS: <Unknown>
        (D) TOPOLOGY: linear (ii) MOLECULE TYPE: peptide (iii) HYPOTHETICAL: yes (v) FRAGMENT TYPE: internal (vi) ORIGINAL SOURCE:
        (A) ORGANISM: <Unknown>

(ix) FEATURE:
        (D) OTHER INFORMATION:hybrid peptide for human papilloma
            virus vaccine (xi) SEQUENCE DESCRIPTION: SEQ ID NO: 17:

His Trp Asp Phe Ala Trp Pro Trp Gly Ser Gly Gly
                5                  10

Leu His Cys Tyr Glu Gln Leu Val
          15                  20

(2) INFORMATION FOR SEQ ID NO: 18:

(i) SEQUENCE CHARACTERISTICS:
        (A) LENGTH: 20
        (B) TYPE: amino acid
        (C) STRANDEDNESS: <Unknown>
        (D) TOPOLOGY: linear (ii) MOLECULE TYPE: peptide (iii) HYPOTHETICAL: yes (v) FRAGMENT TYPE: internal (vi) ORIGINAL SOURCE:
        (A) ORGANISM: <Unknown>

(ix) FEATURE:
        (D) OTHER INFORMATION:hybrid peptide for human papilloma
            virus vaccine
```

(xi) SEQUENCE DESCRIPTION: SEQ ID NO: 18:

Pro Leu Lys Gln His Phe Gln Ile Val Gly Ser Gly
                 5                   10

His Trp Asp Phe Ala Trp Pro Trp
         15                  20

(2) INFORMATION FOR SEQ ID NO: 19:

(i) SEQUENCE CHARACTERISTICS:
        (A) LENGTH: 20
        (B) TYPE: amino acid
        (C) STRANDEDNESS: <Unknown>
        (D) TOPOLOGY: linear (ii) MOLECULE TYPE: peptide (iii) HYPOTHETICAL: yes (v) FRAGMENT TYPE: internal (vi) ORIGINAL SOURCE:
        (A) ORGANISM: <Unknown>

(ix) FEATURE:
        (D) OTHER INFORMATION:hybrid peptide for human papilloma
            virus vaccine (xi) SEQUENCE DESCRIPTION: SEQ ID NO: 19:

His Trp Asp Phe Ala Trp Pro Trp Gly Ser Gly Pro
                 5                   10

Leu Lys Gln His Phe Gln Ile Val
         15                  20

(2) INFORMATION FOR SEQ ID NO: 20:

(i) SEQUENCE CHARACTERISTICS:
        (A) LENGTH: 32
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
        (A) ORGANISM: <Unknown>

(ix) FEATURE:
        (D) OTHER INFORMATION: amplification primer for gp96

(xi) SEQUENCE DESCRIPTION: SEQ ID NO: 20:

AGATATACAT ATGGATGATG AAGTCGACGT GG                                      32

(2) INFORMATION FOR SEQ ID NO: 21:

(i) SEQUENCE CHARACTERISTICS:
        (A) LENGTH: 35
        (B) TYPE: nucleic acid
        (C) STRANDEDNESS: single
        (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
            (A) ORGANISM: <Unknown>

(ix) FEATURE:
            (D) OTHER INFORMATION: amplification primer for gp96

(xi) SEQUENCE DESCRIPTION: SEQ ID NO: 21:

TCGGATCCTT ACAATTCATC CTTCTCTGTA GATTC                                    35

(2) INFORMATION FOR SEQ ID NO: 22:

(i) SEQUENCE CHARACTERISTICS:
            (A) LENGTH: 29
            (B) TYPE: nucleic acid
            (C) STRANDEDNESS: single
            (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
            (A) ORGANISM: <Unknown>

(ix) FEATURE:
            (D) OTHER INFORMATION: amplification primer for gp96

(xi) SEQUENCE DESCRIPTION: SEQ ID NO: 22:

TCGGATCCTT ACTCTGTAGA TTCCTTTTC                                           29

(2) INFORMATION FOR SEQ ID NO: 23:

(i) SEQUENCE CHARACTERISTICS:
            (A) LENGTH: 30
            (B) TYPE: nucleic acid
            (C) STRANDEDNESS: single
            (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
            (A) ORGANISM: <Unknown>

(ix) FEATURE:
            (D) OTHER INFORMATION: amplification primer for BiP (xi) SEQUENCE DESCRIPTION: SEQ ID NO: 23:

AGATATGTGG CCATGGAGGA GGAGGACAAG                                          30

(2) INFORMATION FOR SEQ ID NO: 24:

(i) SEQUENCE CHARACTERISTICS:
            (A) LENGTH: 28
            (B) TYPE: nucleic acid
            (C) STRANDEDNESS: single
            (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
              (A) ORGANISM: <Unknown>

(ix) FEATURE:
              (D) OTHER INFORMATION: amplification primer for BiP (xi) SEQUENCE DESCRIPTION: SEQ ID NO: 24:

TCGGATCCCT ACAACTCATC TTTTTCTG                                              28

(2) INFORMATION FOR SEQ ID NO: 25:

(i) SEQUENCE CHARACTERISTICS:
              (A) LENGTH: 32
              (B) TYPE: nucleic acid
              (C) STRANDEDNESS: single
              (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
              (A) ORGANISM: <Unknown>

(ix) FEATURE:
              (D) OTHER INFORMATION: amplification primer for BiP (xi) SEQUENCE DESCRIPTION: SEQ ID NO: 25:

TCGGATCCCT ATTCTGATGT ATCCTCTTCA CC                                         32

(2) INFORMATION FOR SEQ ID NO: 26:

(i) SEQUENCE CHARACTERISTICS:
              (A) LENGTH: 27
              (B) TYPE: nucleic acid
              (C) STRANDEDNESS: single
              (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
              (A) ORGANISM: <Unknown>

(ix) FEATURE:
              (D) OTHER INFORMATION: amplification primer for hsp40

(xi) SEQUENCE DESCRIPTION: SEQ ID NO: 26:

CCGCAGGAGG GGCATATGGG TAAAGAC                                               27

(2) INFORMATION FOR SEQ ID NO: 27:

(i) SEQUENCE CHARACTERISTICS:
              (A) LENGTH: 26
              (B) TYPE: nucleic acid
              (C) STRANDEDNESS: single
              (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
             (A) ORGANISM: <Unknown>

(ix) FEATURE:
             (D) OTHER INFORMATION: amplification primer for hsp40

(xi) SEQUENCE DESCRIPTION: SEQ ID NO: 27:

GAGGGTCTCC ATGGAATGTG TAGCTG                                            26

(2) INFORMATION FOR SEQ ID NO: 28:

(i) SEQUENCE CHARACTERISTICS:
             (A) LENGTH: 9
             (B) TYPE: amino acid
             (C) STRANDEDNESS: <Unknown>
             (D) TOPOLOGY: linear (ii) MOLECULE TYPE: peptide (iii) HYPOTHETICAL: no (v) FRAGMENT TYPE: internal (vi) ORIGINAL SOURCE:
             (A) ORGANISM: human (ix) FEATURE:
             (D) OTHER INFORMATION: HLA-A2 peptide binding motif (xi) SEQUENCE DESCRIPTION: SEQ ID NO: 28:

Xaa Xaa Xaa Xaa Xaa Xaa Xaa Xaa Leu
              5

(2) INFORMATION FOR SEQ ID NO: 29:

(i) SEQUENCE CHARACTERISTICS:
             (A) LENGTH: 7
             (B) TYPE: amino acid
             (C) STRANDEDNESS: <Unknown>
             (D) TOPOLOGY: linear (ii) MOLECULE TYPE: peptide (iii) HYPOTHETICAL: no (v) FRAGMENT TYPE: internal (vi) ORIGINAL SOURCE:
             (A) ORGANISM: human (ix) FEATURE:
             (D) OTHER INFORMATION: positions 1, 3, 5 and 7 are hydrophobic
                 amino acid residues.
             (D) OTHER INFORMATION: motif (xi) SEQUENCE DESCRIPTION: SEQ ID NO: 29:

Xaa Xaa Xaa Xaa Xaa Xaa Xaa
              5

(2) INFORMATION FOR SEQ ID NO: 30:

(i) SEQUENCE CHARACTERISTICS:
             (A) LENGTH: 7
             (B) TYPE: amino acid
             (C) STRANDEDNESS: <Unknown>

```
             (D) TOPOLOGY: linear (ii) MOLECULE TYPE: peptide (iii) HYPOTHETICAL: no (v) FRAGMENT TYPE: internal (vi) ORIGINAL SOURCE:
             (A) ORGANISM: human (ix) FEATURE:
             (D) OTHER INFORMATION: positions 1, 3, 5 and 7 are
                  independently selected from the group consisting of Trp,
                  Leu and Phe.
             (D) OTHER INFORMATION: motif (xi) SEQUENCE DESCRIPTION: SEQ ID NO: 30:

Xaa Xaa Xaa Xaa Xaa Xaa Xaa
                           5
```